US012611342B2

(12) United States Patent
Remus et al.

(10) Patent No.: US 12,611,342 B2
(45) Date of Patent: Apr. 28, 2026

(54) ABSORBENT ARTICLE PACKAGES WITH NATURAL FIBERS AND OPENING FEATURES

(71) Applicant: The Procter & Gamble Company, Cincinnati, OH (US)

(72) Inventors: Michael Remus, Heidelberg (DE); Naomi Ruth Nelson, Cincinnati, OH (US); Lee Mathew Arent, Fairfield, OH (US); Edward Daniel Theiss, III, Union Township, OH (US); Stephan Spiekers, Frankenhardt (DE); Victoria Anne Borchert, West Chester, OH (US); Peter Kramkowski, Bad Soden am Taunus (DE); Michael Wayne Taylor, Cincinnati, OH (US); Benjamin Jacob Clare, Cincinnati, OH (US); Emily Charlotte Boswell, Cincinnati, OH (US); Nery Vanesa Breslin, Hamilton, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 56 days.

(21) Appl. No.: 18/944,083

(22) Filed: Nov. 12, 2024

(65) Prior Publication Data

US 2025/0064652 A1 Feb. 27, 2025

Related U.S. Application Data

(63) Continuation of application No. 17/496,870, filed on Oct. 8, 2021, now Pat. No. 12,178,692.

(Continued)

(51) Int. Cl.
*A61F 13/551* (2006.01)

(52) U.S. Cl.
CPC ................................. *A61F 13/551* (2013.01)

(58) Field of Classification Search
CPC . A61F 13/551; B65D 65/466; B65D 75/5805; B65D 75/5816; B65D 75/5827; B65D 85/07
See application file for complete search history.

(56) References Cited

U.S. PATENT DOCUMENTS 3,038,651 A * 6/1962 Cloudsley .......... B65D 75/5805
383/106
3,979,049 A 9/1976 Achelpohl
(Continued)

FOREIGN PATENT DOCUMENTS

CN 102048615 A 5/2011
EP 3168362 A1 5/2017
(Continued)

OTHER PUBLICATIONS

"Aegis Paper", Online retrieved from "https://www.nspackaging. com/news/mondi-aegispaper-barrier/"; 2021; 02 pages.
(Continued)

*Primary Examiner* — Orlando E Aviles
*Assistant Examiner* — Jenine Spicer
(74) *Attorney, Agent, or Firm* — Amanda Herman Berghauer; Daniel S. Albrecht

(57) ABSTRACT

A package of one or more absorbent articles is disclosed. The package includes a package material enclosing the one or more absorbent articles. The package material has natural fibers and forms a front panel, a back panel opposite the front panel, a first side panel, a second side panel opposite the first side panel, a top panel, and a bottom panel opposite the top panel. The panels define an interior compartment. The package material has a Basis Weight of between about 55 gsm and about 115 gsm, according to the Basis Weight (Continued)

Test Method. The package has a weakened region. The package is sealed such that the one or more absorbent articles are enclosed in the interior compartment.

20 Claims, 24 Drawing Sheets

Related U.S. Application Data

(60) Provisional application No. 63/089,661, filed on Oct. 9, 2020.

(56) References Cited

U.S. PATENT DOCUMENTS

| | | | |
|---|---|---|---|
| 4,966,286 A | | 10/1990 | Muckenfuhs |
| 5,065,868 A | | 11/1991 | Cornelissen |
| 5,934,470 A | | 8/1999 | Bauer et al. |
| 5,967,665 A | * | 10/1999 | MacDonald ......... B65D 75/522 |
| | | | 383/207 |
| 6,026,957 A | | 2/2000 | Bauer et al. |
| 6,229,061 B1 | | 5/2001 | Dragoo |
| 8,152,902 B2 | | 4/2012 | Wood et al. |
| 9,827,150 B1 | * | 11/2017 | Sheehan ............... B65D 85/07 |
| 10,786,404 B2 | | 9/2020 | Cheng et al. |
| 11,439,544 B2 | | 9/2022 | Ehrnsperger et al. |
| 12,076,221 B2 | | 9/2024 | Remus |
| 12,178,692 B2 | | 12/2024 | Remus et al. |
| 2002/0148749 A1 | | 10/2002 | Briseboi et al. |
| 2003/0106825 A1 | | 6/2003 | Molina et al. |
| 2004/0146224 A1 | | 7/2004 | Piotrowski et al. |
| 2004/0232024 A1 | | 11/2004 | Guerreschi |
| 2006/0096880 A1 | * | 5/2006 | Zander ............... B65D 83/0811 |
| | | | 206/440 |
| 2006/0191985 A1 | | 8/2006 | Norcom |
| 2007/0099542 A1 | | 5/2007 | Sakaguchi et al. |
| 2007/0230834 A1 | | 10/2007 | Schneider |
| 2008/0128309 A1 | | 6/2008 | Snell |
| 2008/0142404 A1 | | 6/2008 | Snell |
| 2009/0145792 A1 | | 6/2009 | Lewis |
| 2010/0150479 A1 | | 6/2010 | Smith |
| 2011/0120897 A1 | * | 5/2011 | Takahashi ......... A61F 13/51496 |
| | | | 206/459.5 |
| 2013/0098793 A1 | | 4/2013 | Noguchi et al. |
| 2013/0156352 A1 | | 6/2013 | Koehn |
| 2014/0348444 A1 | | 11/2014 | Puccini |
| 2017/0057721 A1 | | 3/2017 | Lee et al. |
| 2018/0118436 A1 | * | 5/2018 | Sheehan ............... B65D 85/07 |
| 2018/0177711 A1 | | 6/2018 | El-khouri |
| 2018/0187377 A1 | | 7/2018 | Ziegenbein |
| 2018/0289564 A1 | | 10/2018 | Sheehan |
| 2019/0091077 A1 | | 3/2019 | Cheng et al. |
| 2019/0126603 A1 | | 5/2019 | Zerial |
| 2020/0046579 A1 | | 2/2020 | Sheehan |
| 2020/0063367 A1 | | 2/2020 | Parker et al. |
| 2020/0354129 A1 | | 11/2020 | Sheehan et al. |
| 2022/0110801 A1 | | 4/2022 | Remus et al. |
| 2024/0358560 A1 | | 10/2024 | Remus |

FOREIGN PATENT DOCUMENTS

| | | | |
|---|---|---|---|
| EP | 3632812 A1 | 4/2020 | |
| EP | 3633104 A1 | 4/2020 | |
| JP | S58160033 A | 9/1983 | |
| JP | 3094949 B2 | 10/2000 | |
| JP | 2005145561 A | 6/2005 | |
| JP | 2007262603 A | 10/2007 | |
| JP | 2011020711 A | 2/2011 | |
| JP | 2014198588 A | 10/2014 | |
| WO | 9210412 A1 | 6/1992 | |
| WO | 2009011326 A1 | 1/2009 | |
| WO | 2019056351 A1 | 3/2019 | |
| WO | 2021165317 A1 | 8/2021 | |
| WO | 2021200656 A1 | 10/2021 | |

OTHER PUBLICATIONS

"Kraft paper", Online retrieved from "https://en.wikipedia.org/wiki/Kraft_paper"; Unknown date;03 pages.

"Wax Paper", Online retrieved from "https://en.wikipedia.org/wiki/Waxed_paper"; Unknown date; 02 pages.

15890MQ PCT Search Report and Written Opinion for PCT/US2021/054073 dated Mar. 10, 2022, 13 pages.

All Office Actions; U.S. Appl. No. 17/389,487, filed Jul. 30, 2021.

All Office Actions; U.S. Appl. No. 17/496,870, filed Oct. 8, 2021.

All Office Actions; U.S. Appl. No. 18/753,258, filed Jun. 25, 2024.

Axello Tough White White MF Kraft Paper. Technical Datasheet [online]. BillerudKorsnäs Axello, Sep. 12, 2019 retrieved on Jul. 27, 2022]. Retrieved from the Internet: https://www. billerudkorsnas. com/packaging-materials/kraft-paper-bags/ axello (Year: 2019), pp. 12.

* cited by examiner

MD

CD

100

90

99

110

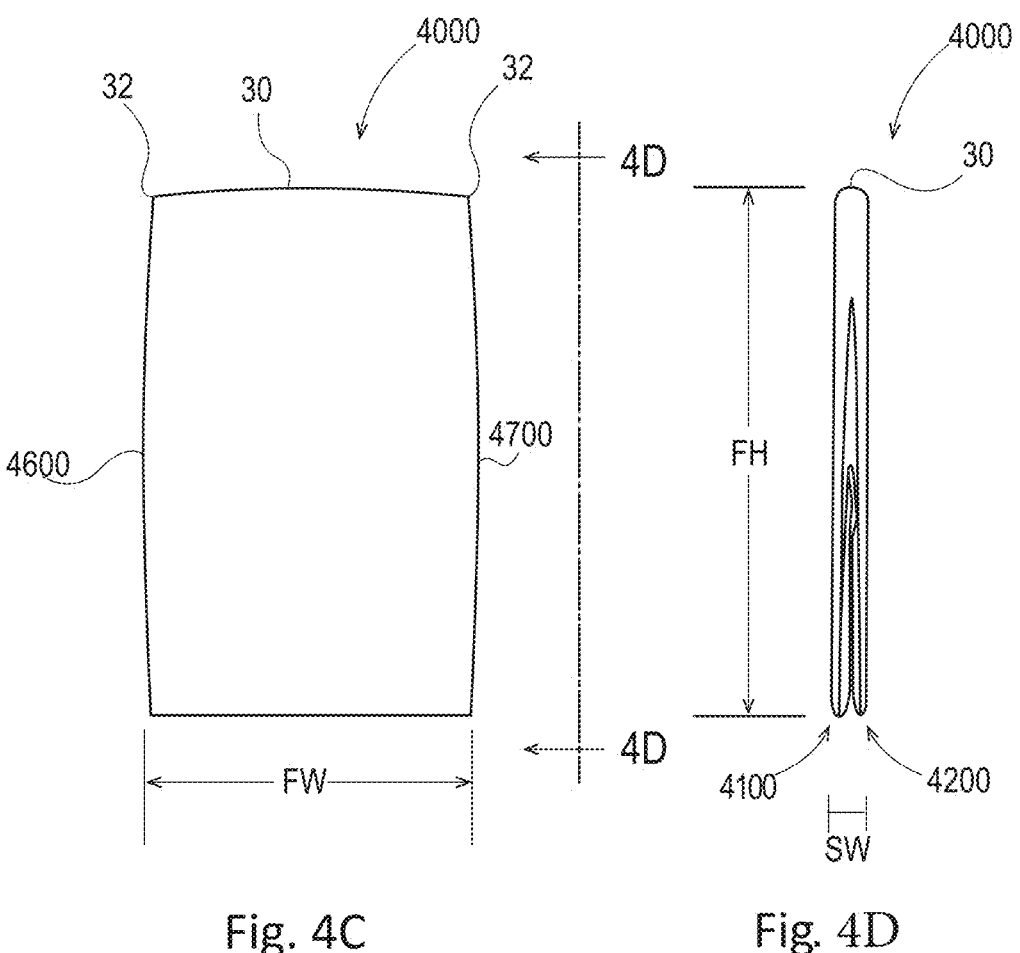
Fig. 4C                    Fig. 4D

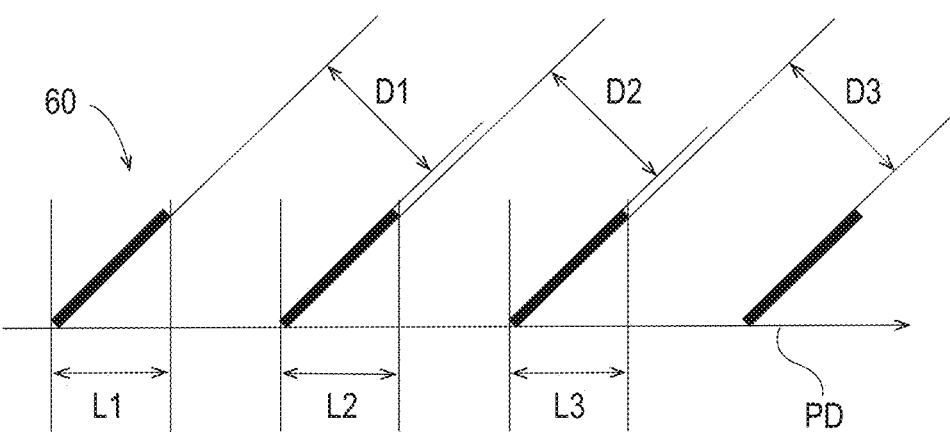
Fig. 8
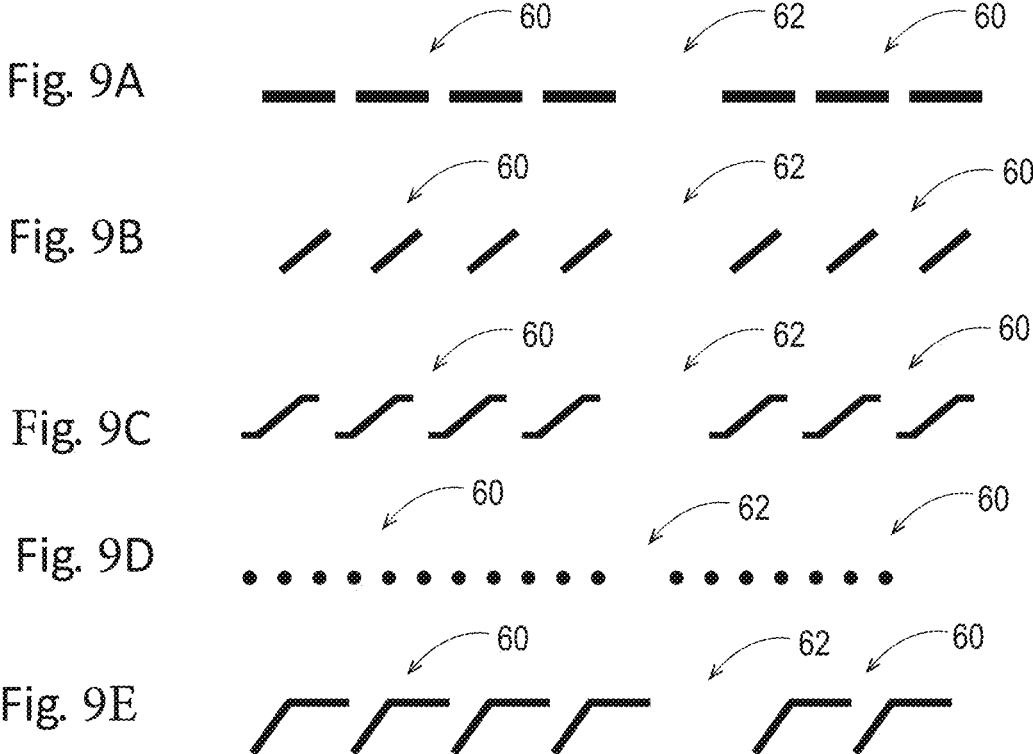

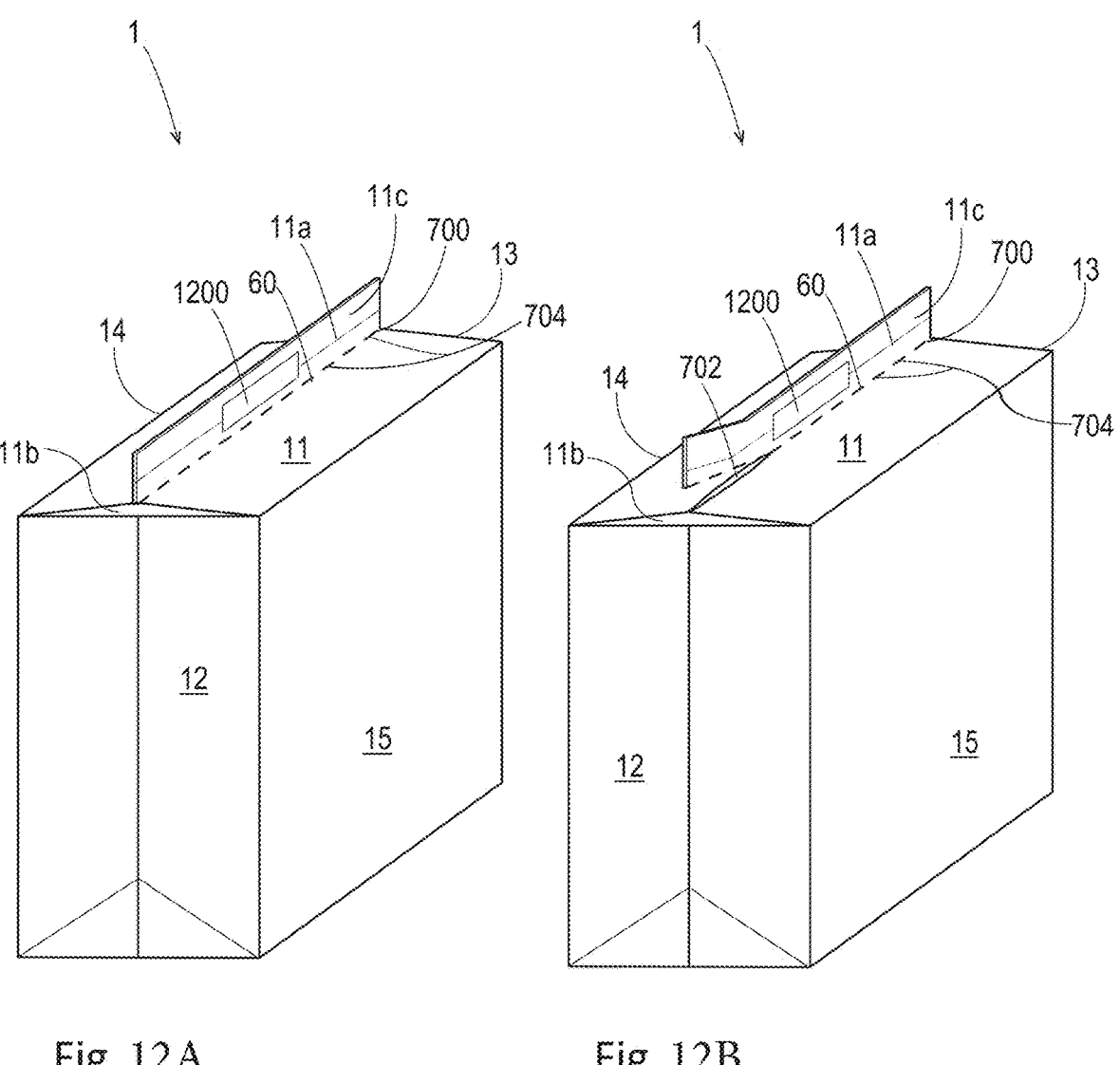
Fig. 12A                  Fig. 12B

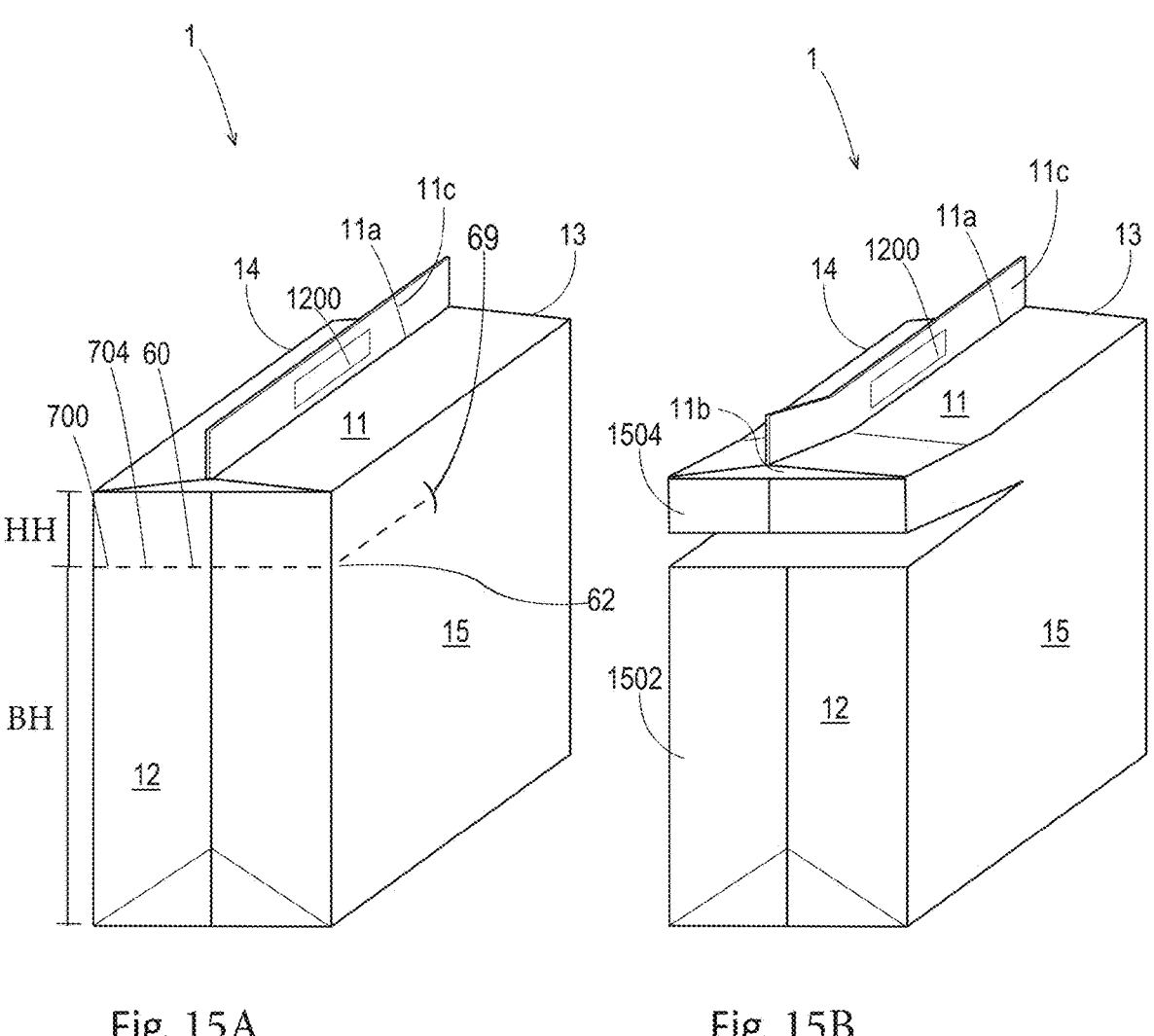
Fig. 15A                    Fig. 15B

ABSORBENT ARTICLE PACKAGES WITH NATURAL FIBERS AND OPENING FEATURES

CROSS REFERENCE TO RELATED APPLICATION

This application is a continuation of U.S. patent application Ser. No. 17/496,870 filed on Oct. 8, 2021, which claims the benefit, under 35 U.S.C. § 119(e), of U.S. Provisional Patent Application Ser. No. 63/089,661, filed on Oct. 9, 2020, which is incorporated herein by reference in its entirety.

FIELD

The present disclosure is directed to absorbent article packages, more particularly to absorbent article packages with natural fibers and opening features.

BACKGROUND

Consumer demand for products made at least partially from renewable resources has increased significantly over the past decade, and has become a driver of innovation for new and improved consumer goods and packaging materials. As such, there is an increased focus on products and packaging materials comprising renewable resources. For example, there is a strong desire in the marketplace for consumer products that comprise natural and bio-sourced materials, recyclable materials, recycled materials, and/or biodegradable materials.

Non-fragile, compressible consumer products such as disposable absorbent articles (e.g., diapers and training pants, disposable adult incontinence pants and feminine hygiene pads) are often packaged and sold at retail in soft packages formed of plastic polymer film. Plastic is preferred as the primary package of consumer goods because plastic may withstand the rigors of a packaging process, given plastic's ability to flex and stretch. In addition, because plastic can flex and stretch without tearing upon the application of force, opening features disposed in plastic packages, tend to form clean openings while preserving the integrity of the rest of the package. Plastic packages, however, tend not to retain their shape, and may collapse upon removal of articles.

Packages comprising renewable resources, such as natural fibers (e.g., carton board, cardboard, and paper), may be prone to creasing, cracking, and tearing under packaging processes and opening strain. Therefore, packaging materials comprising renewable resources, such as natural fibers, for absorbent articles should be improved.

SUMMARY

The present disclosure solves one or more of the problems discussed above by providing a package of one or more absorbent articles comprising a package material made at least partially from renewable resources and comprising an opening feature. The package material, including the opening feature, may withstand the rigors of a packaging process, shipment, and handling on shelf and at a consumer's home. The opening feature may allow for the package made at least partially from renewable resources to maintain its shape after opening and partial dispensing.

The present disclosure provides, in part, a package of one or more absorbent articles comprising a package material, wherein the package material comprises natural fibers. The package material forms a front panel, a back panel opposite the front panel, a first side panel, a second side panel opposite the first side panel, a top panel, and a bottom panel opposite the top panel, wherein the panels define an interior compartment. The one or more absorbent articles are disposed in the interior compartment. The package material has a Basis Weight between about 50 gsm and about 120 gsm, preferably between about 55 gsm and about 115 gsm, or more preferably between about 60 gsm and about 110 gsm, according to the Basis Weight Test Method described herein. The package comprises a weakened region comprising perforations disposed in the package material configured to form an opening. The weakened region is disposed on at least a portion of the top panel or a top edge region of the top panel. The package is sealed such that the one or more absorbent articles are enclosed within the interior compartment. The package has a Weakened Region Performance Factor of between 0.14:1 and 0.98:1, according to the Strength Tensile Test Method.

The present disclosure provides, in part, a package of one or more absorbent articles comprising a package material, wherein the package material comprises natural fibers. The package material forms a front panel, a back panel opposite the front panel, a first side panel, a second side panel opposite the first side panel, a top panel, and a bottom panel opposite the top panel, wherein the panels define an interior compartment. The one or more absorbent articles are disposed in the interior compartment. The package material has a Basis Weight between about 50 gsm and about 120 gsm, preferably between about 55 gsm and about 115 gsm, or more preferably between about 60 gsm and about 110 gsm, according to the Basis Weight Test Method described herein. The package comprises a weakened region comprising perforations disposed in the package material configured to form an opening. The weakened region is disposed on at least a portion of the top panel or a top edge region of the top panel. The package is sealed such that the one or more absorbent articles are enclosed within the interior compartment. The package has a Weakened Region Performance Factor of between 0.14:1 and 0.98:1, according to the Strength Tensile Test Method, and a Tear Performance Factor of between 0.865 and 5.16, according to the Tear Tensile Test Method

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein:

FIG. 4C is a plan view of the diaper of FIG. 4B, shown folded about a lateral fold line, wearer-facing surfaces in and outward-facing surfaces out;

FIG. 4D is a side view of the folded diaper shown in FIG. 4C;

FIG. 8 is a schematic plan view depiction of an example of a configuration of perforations, illustrating measurements for determining cut-to-land ratio;

FIGS. 9A-9E are schematic plan view depictions of examples of configurations of perforations comprising registered land areas;

FIG. 12A is a perspective view of a package of the present disclosure, depicting a weakened region disposed between the closing seam and the interior compartment in a closed configuration;

FIG. 12B depicts the package of FIG. 12A in a partially open configuration;

FIG. 15A is a perspective view of a package of the present disclosure, depicting a weakened region disposed on at least a portion of the front, back, and one of the first or second side panels (long-short-long) and forming a base and a hood;

FIG. 15B depicts the package of FIG. 15A in a partially open configuration;

DETAILED DESCRIPTION

Figure 1A:
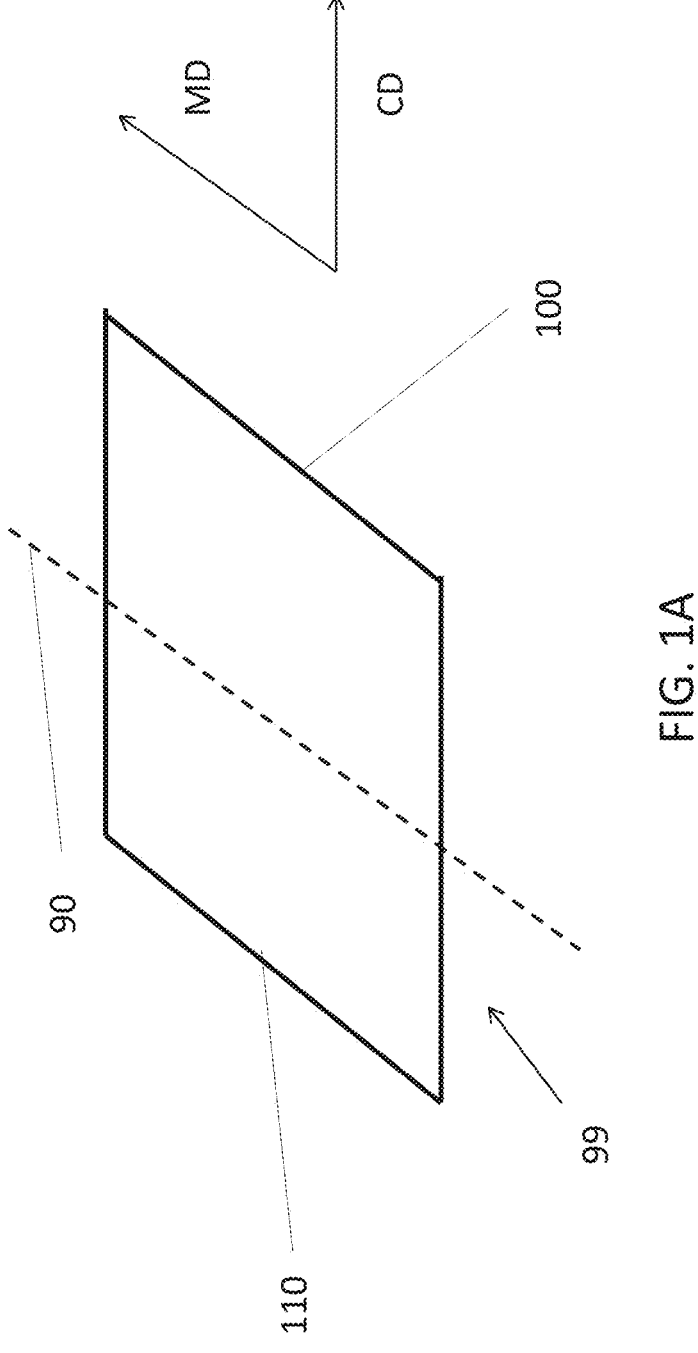
FIG. 1A is a schematic representation of a package material sheet.

The term "absorbent article", as used herein, refers to devices which absorb and contain exudates, and, more specifically, refers to devices which are placed against or in proximity to the body of the wearer to absorb and contain the various exudates discharged from the body. Absorbent articles of the present disclosure include, but are not limited to, diapers, adult incontinence briefs, training pants, diaper holders, menstrual pads, incontinence pads, liners, absorbent inserts, pantiliners, tampons, and the like.

The term "machine direction" or "MD", as used herein, refers to a path that material, such as a package material, follows through a manufacturing process.

The term "cross-machine direction" or "CD", as used herein, refers to a path that is perpendicular to the machine direction in the plane of the material.

The term "natural fibers" as used herein, refers to fibers which comprise cellulose-based fibers, bamboo fibers, and the like. Natural fibers also refers to: nonwoody fibers, such as cotton, abaca, kenaf, sabai grass, flax, esparto grass, straw, jute, hemp, bagasse, milkweed floss fibers, and pineapple leaf fibers; and woody fibers, such as wood or pulp fibers such as those obtained from deciduous and coniferous trees, including softwood fibers, such as northern and southern softwood kraft fibers, hardwood fibers, such as *eucalyptus*, maple, birch, and aspen. Pulp fibers may be prepared in high-yield or low-yield forms and may be pulped in any known method, including kraft, sulfite, high-yield pulping methods and other known pulping methods. The natural fibers of the present disclosure may be recycled natural fibers, virgin natural fibers or mixes thereof. Additionally, for good mechanical properties in natural fibers, it may be desirable that the natural fibers be relatively undamaged and largely unrefined or only lightly refined. The fibers may have a Canadian Standard Freeness of at least 200, more specifically at least 300, more specifically still at least 400, and most specifically at least 500.

The term "cellulose-based fibers," as used herein, may include regenerated cellulose fiber such rayon or cuprammonium rayon, and high pulping yield fibers, unless specified differently. The term "cellulose-based fibers" also includes chemically treated natural fibers, such as mercerized pulps, chemically stiffened or crosslinked fibers, or sulfonated fibers. Also included are mercerized natural fibers, regenerated natural cellulosic fibers, cellulose produced by microbes, the rayon process, cellulose dissolution and coagulation spinning processes, and other cellulosic material or cellulosic derivatives. Other cellulose-based fibers included are paper broke or recycled fibers and high yield pulp fibers. High yield pulp fibers are those fibers produced by pulping processes providing a yield of about 65% or greater, more specifically about 75% or greater, and still more specifically about 75% to about 95%. Yield is the resulting amount of processed fibers expressed as a percentage of the initial wood mass. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which leave the resulting fibers with high levels of lignin but are still considered to be natural fibers. High yield fibers are well known for their stiffness in both dry and wet states relative to typical chemically pulped fibers.

The package of the present disclosure comprises a package material containing absorbent articles wherein the package material comprises or is derived from natural resources. Namely, the package material of the present disclosure comprises natural fibers. The natural fibers may form a paper from which the package material is made. The composition of the package materials is discussed in additional detail herein.

Package Materials

The package materials of the present disclosure comprise natural fibers. The package materials of the present disclosure may comprise wood fiber and/or pulp fiber. The package materials may comprise at least 50 percent by weight natural fibers, at least 70 percent by weight natural fibers, at least 90 percent by weight natural fibers, between about 50 percent and about 100 percent by weight natural fibers, between about 65 percent and about 99 percent by weight natural fibers, or between about 75 percent and about 95 percent by weight of natural fibers, specifically reciting all values within these ranges and any ranges formed therein or thereby. In one form, the package materials may comprise 99.9% percent by weight natural fibers.

Inks and/or dyes associated with the package art, branding, package information, and/or background color, as well as adhesives associated with the seams and barrier coatings are also considered part of the package materials on a weight percentage basis. Where the weight percentage of natural fibers is less than 100 percent, the difference may be made up by inks, dyes, and/or adhesives. Inks, dyes, coatings, and adhesives may be considered contaminants in a paper recycling process, but may be otherwise recyclable.

While the package materials may comprise many different fibers, inks, dyes, coatings, adhesives, etc., the package material of the present disclosure may be constructed to facilitate and/or encourage recycling of the package material, and may encourage recycling of the package material within a single recycling stream, such as a paper recycling stream. Whether package materials are recyclable may vary from region to region. In order to meet one of the highest standards for recyclability, the total weight percentage of non-recyclable material, including material not recyclable within a particular recycling stream—such as a paper recycling stream—but otherwise recyclable, e.g. inks, dyes, adhesives, and coatings in the package material may be 5 percent by weight of the package material or less, or between 0.1 percent to 5 percent by weight, specifically reciting all values within these ranges and any ranges formed therein. However, other jurisdictions may allow a higher weight percentage of non-recyclable material. For example, in other jurisdictions, the package material of the present disclosure may comprise 50 percent by weight or less, 30 percent by weight or less, or about 15 percent by weight or less of non-recyclable material, specifically including all values within these ranges and any ranges formed therein or thereby. As another example, the package materials of the present disclosure may comprise from between about 0.1 percent to about 50 percent by weight, from about 0.1 percent to about 30 percent by weight, or from about 0.1 percent to about 15 percent by weight of non-recyclable material, specifically including all values within these ranges and any ranges formed therein or thereby. In an example, the amount of inks, dyes, coatings, and adhesives is 5 percent by weight, or less, or between 0.1 percent by weight to 5 percent by weight, specifically reciting all values within these ranges and any ranges formed therein.

The package materials of the present disclosure may be free of a barrier layer. As used herein, the term "barrier layer" refers to a layer of material, including barrier coatings, barrier plastics, and/or barrier foils, that is joined to the package materials comprising natural fibers. Such barrier layers may reduce the recyclability of the package materials within a single recycling stream.

In other instances, in order to at least partially protect absorbent articles disposed within the package, the package materials of the present disclosure may comprise a barrier layer. The barrier layer may at least partially inhibit the migration of water vapor through the package material. The barrier layer may comprise a water soluble material that may not interfere with a recycling process. The barrier layer may be easily separable from the remainder of the package materials through a recycling process, for example by having a different water solubility, density, buoyancy, or other physical features as compared to the remainder of the package materials.

The type of adhesives utilized for the seals of the packages of the present disclosure may impact the recyclability of the package as well. As an example, adhesives that can dissolve in water during the re-pulping step or the disintegration step of the paper recycling process may be particularly suitable for the packages of the present disclosure. Such adhesives include starch based adhesives, polyvinyl acetate based adhesives, and polyethylene oxide based adhesives. A suitable example of a starch based adhesive is available from LD Davis located in Monroe, North Carolina, under the trade name AP0420CR. A suitable example of a polyvinyl acetate based adhesive is available from Sekisui Chemical Company, located in Osaka, Japan, under the trade name Selvol 205. A suitable example of a polyethylene oxide based adhesive is available from Dow Chemicals Co. located in Midland, Michigan, under the trade name WSR N-80.

Water-dispersible adhesives may similarly be utilized. Suitable examples of water dispersible adhesives include thermoplastic elastomer based adhesives and polyvinyl acetate based adhesives. A suitable example of a thermoplastic elastomer based adhesive is available from Actega located in Blue Ash, Ohio, under the trade name Yunico 491. A suitable example of a polyvinyl acetate based adhesive is available from Bostik located in Milwaukee, Wisconsin, under the trade name Aquagrip 4419U01. Another suitable example of a polyvinyl acetate based adhesive is available from HB Fuller under the trade name PD-0330.

Without wishing to be bound by theory, it is believed that packages of the present disclosure which utilize adhesives dissolvable in water may comprise a higher weight percentage of such adhesives than adhesive which are only water dispersible. For example, packages comprising water dissolvable adhesives may comprise a first weight percentage of adhesive while packages comprising water dispersible adhesives may comprise a second weight percentage of adhesive. The first weight percentage may be greater than the second weight percentage for the purposes of recycling the package material.

Where a barrier layer is utilized, the barrier material may be selected such that the use of adhesives can be reduced or eliminated. One such barrier material may be polyethylene film coated on an inner surface of the package material. The polyethylene may be utilized to form the seals rather than an adhesive or in conjunction with an adhesive. However, as the polyethylene film may not be recyclable in the same stream as the other package materials, the weight percentage of the polyethylene may be in accordance with the present description regarding percentages of non-recyclable material discussed herein.

The effectiveness of the recycling process on the package material of the present disclosure may be determined via recyclable percentage. Package material of the present disclosure may exhibit recyclable percentages of 60 percent or greater, 75 percent or greater, or 90 percent or greater, specifically reciting all values within these ranges and any ranges formed therein or thereby. The packaging material of the present disclosure may have a recyclable percentage of between about 60 percent and about 99.9 percent, between about 75 percent and about 99.9 percent, or between about 90 percent and about 99.9 percent, specifically reciting all values within these ranges and any ranges formed therein or thereby. In a specific example, the package material of the present disclosure may exhibit a recyclable percentage of between about 95 percent and about 99.9 percent, specifically including all values within these ranges and any ranges formed therein. The recyclable percentage of the package material of the present disclosure is determined via test PTS-RH:021/97 (Draft October 2019) under category II, as performed by Papiertechnische Stiftung located at Pirnaer Strasse 37, 01809 Heidenau, Germany.

Along with recyclable percentage, the total reject percentage is determined via the PTS-RH:021/97 (Draft October 2019) under category II Test Method. The total reject percentage of the package material of the present disclosure may be 40 percent or less, 30 percent or less, or 10 percent or less, specifically including all values within these ranges and any ranges formed therein or thereby. For example, the total rejection percentage of the package material of the present disclosure may be from about 0.5 percent to about 40 percent, from about 0.5 percent to about 30 percent, or from about 0.5 percent to about 10 percent, specifically reciting all values within these ranges and any ranges formed therein or thereby.

It is believed that the percent non-recyclable material does not necessarily have a 1:1 correlation to the total reject percentage. For example, dissolvable adhesives and/or coatings are designed to dissolve during the recycling process. It is theorized that these adhesive may not have an impact the total reject percentage; however, they would contribute to the non-recyclable material weight percent.

The PTS-RH:021/97 (Draft October 2019) under category II Test Method also comprises a visual component. Trained screeners inspect one or more handsheets of recycled package material for visual imperfections. If the number of visual imperfections is too great, then the package material is rejected. If the number of visual imperfections is acceptable, in accordance with the PTS-RH:021/97 (Draft October 2019) under category II Test Method, then the package material is approved for additional processing. The package material of the present disclosure may yield an acceptable level of visual imperfections during this step of the method.

The package material of the present disclosure may yield the recyclable percentages mentioned heretofore as well as pass the visual screening method. Thus, the package material of the present disclosure may achieve an overall score or final outcome of "pass" when subjected to the PTS-RH:021/97 (Draft October 2019) under category II Test Method.

It is also worth noting that there is an alternative method for determining the recyclable percentage of the package material of the present disclosure. The Test Method performed by the University of Western Michigan, called the Repulpability Test Method, may provide a percent yield of recyclable material. While there are subtle differences between the Repulpability Test Method performed by Western Michigan and the PTS-RH:021/97 (Draft October 2019) under category II Test Method, it is believed that the percentage yield of the Repulpability Test Method would be similar to the recyclable percentage provided by the PTS Test Method.

It is contemplated that the package material of the present disclosure, while being recyclable, may itself comprise recycled material. Such determination can be made from a visual inspection of the package. For example, manufacturers typically advertise the use of recycled materials in an effort to demonstrate their eco-friendly product approach. To further expand on this example, some manufacturers may utilize a logo, e.g., a leaf, along with wording to indicate the use of recycled material in the package material. Often times, manufacturers may specify the percentage of recycled material utilized as well, e.g., over 50 percent, over 70 percent, etc.

Visual inspection may be as simple as utilizing the human eye to inspect packages for logos of the use of recycled material. Additionally, or alternatively, visual inspection may include microscopy methods such as optical microscopy, scanning electron microscopy or other suitable methods known in the art. For example, package material comprising recycled paper fibers may appear different under a microscope due to the presence of a much wider range of natural fiber types than if the package material comprised of 100% non-recycled paper. As another example, under a microscope, recycled fibers—due to their increased processing—may appear more fibrillated than their virgin fiber counterparts.

In order to withstand the rigors of a high speed manufacturing process where a plurality of absorbent articles are placed within the package, withstand the force of compressed absorbent articles being placed directly into the package without an intermediate package or container, withstand the rigors of being shipped, provide protection from environmental insults during shipping and while on the store shelf, and provide for product protection while in the consumers home, the package materials may have some level of strength, stretch, and/or resilience. The package materials of the present disclosure may be characterized using metrics such as: MD Tensile Strength in kN/m, CD Tensile Strength in kN/m, MD Stretch At Break in percent, CD Stretch At Break in percent, Burst Strength in kPa, Caliper in $\mu$m, MD Tensile Energy Absorption in J/m$^2$, CD Tensile Energy Absorption in J/m$^2$, and Basis Weight in grams per square meter. While all of the metrics may be utilized together to characterize the package materials of the present disclosure, it is believed that some of the metrics alone or in conjunction with others may suffice to characterize package materials which are suitable for packaging absorbent articles. As an example, it is believed that the Burst Strength may be utilized alone or in conjunction with other metrics to obtain package materials which are sufficient for packaging of absorbent articles. Similarly, it is believed that the Tensile Energy Absorption (TEA) in the MD and CD may be utilized in conjunction with one another, and if desired, along with any other combination of the above metrics, to obtain package materials which are suitable for packaging of absorbent articles. As yet another example, it is contemplated that MD Stretch At Break and/or CD Stretch At Break may be utilized in conjunction with at least one of MD Tensile Strength or CD Tensile Strength, respectively, to characterize package materials which may be sufficient to package absorbent articles as described herein. Any suitable combination of metrics may be utilized.

The package materials of the present disclosure may have an MD Tensile Strength of at least 5 kN/m, at least 7 kN/m, or at least 8 kN/m, specifically reciting all values within these ranges and any ranges formed therein or thereby. The MD Tensile Strength may be between about 5 kN/m and about 8.5 kN/m, between about 5.2 kN/m and about 8.2 kN/m, or between about 5.5 kN/m and about 8.0 kN/m, specifically reciting all values within these ranges and any ranges formed therein or thereby. The MD Tensile Strength is measured using the Strength Tensile Test Method described herein.

The package materials of the present disclosure may have a CD Tensile Strength of at least 3 kN/m, at least 4 kN/m, or at least 5.5 kN/m, specifically reciting all values within these ranges and any ranges formed therein or thereby. The CD Tensile Strength may be between about 3 kN/m and about 6.5 kN/m, between about 3 kN/m and about 6.2 kN/m, or between about 3 kN/m and about 6 kN/m, specifically reciting all values within these ranges and any ranges formed therein or thereby. The CD tensile strength is measured using the Strength Tensile Test Method.

The package materials of the present disclosure may have a Burst Strength of at least 200 kPa, at least 250 kPa, or at least 550 kPa, specifically reciting all values within these ranges and any ranges formed therein or thereby. The Burst Strength of the package materials of the present disclosure may be between about 200 kPa and about 600 kPa, between about 220 kPa and about 550 kPa, or between about 250 kPa and about 500 kPa, specifically reciting all values within these ranges and any ranges formed therein or thereby. The Burst Strength is measured using the Burst Strength Test Method described herein. It is believed that the Burst Strength, as measured, includes components of strength, flexibility, and resiliency. As such, it is believed that Burst Strength may be used independently from the other metrics mentioned.

The package materials of the present disclosure, in addition to strength, may also exhibit some measure of resiliency. Thus, the package materials of the present disclosure may exhibit an MD Stretch At Break of at least 3 percent, at least 4 percent, or at least 6 percent, specifically reciting all values within these ranges and any ranges formed therein or thereby. The package materials of the present disclosure may exhibit an MD Stretch At Break of between about 3 percent and about 6.5 percent, between about 3.2 percent and about 6.2 percent, or between about 3.5 percent and about 6 percent, specifically reciting all values within these ranges and any ranges formed therein or thereby. The MD Stretch At Break is measured using the Strength Tensile Test Method described herein.

The package materials of the present disclosure may exhibit a CD Stretch At Break of at least 4 percent, at least 6 percent, or at least 9 percent, specifically reciting all values within these ranges and any ranges formed therein or thereby. The package materials of the present disclosure may exhibit a CD Stretch At Break of from about 4 percent and about 10 percent, from about 4.5 percent and about 9.5 percent, or from about 5 percent and about 9 percent, specifically reciting all values within these ranges and any ranges formed therein or thereby. The CD Stretch At Break is measured using the Strength Tensile Test Method described herein.

Regarding Caliper, the package materials of the present disclosure may exhibit a Caliper of at least 50 μm, at least 70 μm, or at least 90 μm, specifically reciting all values within these ranges and any ranges formed therein or thereby. The package materials of the present disclosure may exhibit a Caliper of between about 50 μm and about 110 μm, from about 55 μm and about 105 μm, or from about 60 μm and about 100 μm, specifically reciting all values within these ranges and any ranges formed therein or thereby. Caliper is measured using the Caliper Test Method described herein.

Regarding Tensile Energy Absorption (TEA), the package materials of the present disclosure may exhibit an MD TEA of at least 150 J/m$^2$, greater than 170 J/m$^2$, or at least 180 J/m$^2$, specifically reciting all values within these ranges and any ranges formed therein or thereby. The package materials of the present disclosure may have an MD TEA of between about 100 J/m$^2$ and about 250 J/m$^2$, between about 125 J/m$^2$ and about 225 J/m$^2$, or between about 150 J/m$^2$ and about 200 J/m$^2$, specifically reciting all values within these ranges and any ranges formed therein or thereby.

The package materials of the present disclosure may have a CD TEA of at least 150 J/m$^2$, at least 200 J/m$^2$, or at least 250 J/m$^2$, specifically reciting all values within these ranges and any ranges formed therein or thereby. The package materials of the present disclosure may have a CD TEA of between about 150 J/m$^2$ and about 275 J/m$^2$, from about 175 J/m$^2$ and about 260 J/m$^2$, or between about 200 J/m$^2$ and about 250 J/m$^2$, specifically reciting all values within these ranges and any ranges formed therein or thereby. TEA in the MD and CD are measured according the Strength Tensile Test Method described herein.

The Basis Weight of the package materials may affect the "feel" of the package to the consumer as well as the strength of the package. Too low of a Basis Weight and the package may feel too flimsy. Too high and the package may feel too inflexible. The package materials of the present disclosure have a Basis Weight of between about 50 gsm and about 120 gsm, between about 55 and about 115 gsm, or between about 60 gsm and about 110 gsm, specifically reciting all values within these ranges and any ranges formed therein or thereby. The Basis Weight, also referred to as "grammage", is determined according to the Basis Weight Test Method described herein.

It is worth noting that for high speed packaging processes, the lower Basis Weight of 50 gsm may provide some quality assurance outages. It is believed that high speed packaging processes may cause strain on the packaging materials that slower packaging processes may not. Therefore, where package materials are processed using a high speed manufacturing process, 60 gsm may be the lowest desirable package material Basis Weight. Where package materials are processed using a hand packing process or lower speed packaging processes, 50 gsm may be sufficient as the lowest package material Basis Weight.

The package materials of the present disclosure are different than carton board and cardboard. For example, carton board is not as flexible as the package materials of the present disclosure. Carton board is inherently stiffer than the package materials of the present disclosure and does not have the processability on high speed converting lines as does the package materials of the present disclosure. Additionally, carton board has a Basis Weight greater than 160 gsm, which is considerably higher than that of the package materials of the present disclosure.

Similarly, cardboard is also different than the package materials of the present disclosure. Cardboard has a much higher Basis Weight (greater than 200 gsm) than those of the package materials of the present disclosure. Additionally, cardboard is much less flexible than the package materials of the present disclosure. Cardboard materials are commonly fluted and comprise three plies of a paper material and, as such, are structurally different than the package materials of the present disclosure.

The package materials of the present disclosure have the advantage of being more flexible as compared to carton board and cardboard. Another advantage is that the package materials of the present disclosure take up less space than the more-bulky carton board and cardboard. A further advantage of the package materials of the present disclosure, attributable at least in part to the strength and resiliency properties discussed herein, is that the package materials allow the packaged absorbent articles to be compressed within the package. This allows for more products to fit within a smaller volume package which may increase manufacturing efficiency. One additional advantage is that a single layer (one ply) of the package materials of the present disclosure may form packages of the present disclosure. The inventors have found that, due at least in part to the flexibility, strength, and resiliency properties of the package materials, packages of the present disclosure may be formed from a single layer (one ply) of package materials of the present disclosure.

Despite having reduced flexibility compared to, for example, plastic packaging, and lower Basis Weight than cardboard and carton board, the inventors have surprisingly found the packaging materials of the present disclosure may withstand the rigors of a high speed manufacturing process—where a plurality of absorbent articles are placed within the package under compression—as well as the rigors of being shipped, provide protection from environmental insults during shipping and while on the store shelf, and provide protection for absorbent articles while in the consumers home.

Table 1 shows a variety of package materials which are able to be successfully utilized in packaging absorbent articles under high speed processing conditions, along with at least one package material which is not successful. The various properties discussed previously are also listed for each of the samples.

Sample 1: Packaging paper produced from pure, white kraft pulp and consisting entirely of virgin fibers, available from BillerudKorsnäs™ under the trade name Axello Tough White.

Sample 2: Packaging paper produced from pure, white kraft pulp and consisting entirely of virgin fibers, available from BillerudKorsnäs™ under the trade name Performance White SE.

Sample 3: Calendered specialty kraft paper consisting entirely of virgin fibers, available from Mondi™ under the trade name Advantage Smooth White Strong.

Sample 4: Packaging paper produced from kraft pulp, made of virgin fibers, and comprising a barrier coating of fluoropolymers, available from BillerudKorsnäs™ under the trade name Basix Glaze.

12

TABLE 1

|  | Sample 1 | Sample 2 | Sample 3 | Sample 4 |
|---|---|---|---|---|
| Basis Weight (gsm) | 80 | 70 | 70 | 50 |
| MD Tensile Strength(kN/m) | 7.6 | 5.7 | 5.9 | 4.7 |
| CD Tensile Strength (kN/m) | 4.7 | 4.1 | 3.0 | 2.7 |
| Burst Strength (kPa) | 480 | — | 256 | 185 |
| MD Stretch At Break (%) | 4.5 | 6.0 | 2.5 | — |
| CD Stretch At Break (%) | 8.0 | 9.5 | 8.0 | — |
| Caliper (μm) | 92.0 | — | 89.0 | 67.0 |
| TEA MD (J/m$^2$) | 185 | 230 | — | — |
| TEA CD (J/m$^2$) | 240 | 200 | — | — |

The package material of Sample 4 is not able to be successfully utilized in the packaging of absorbent articles. During the placement of absorbent article in the package, the package material tore. Without wishing to be bound by theory, it is believed that Sample 4 failed due to a combination of low Basis Weight and a high speed packaging process. While Sample 4 failed under the conditions of the high speed process, it is believed that a sample having the properties of Sample 4 may be successful with the use of a gentler packaging process, such as hand packing.

Package Configurations

The package materials of the present disclosure may be arranged as a package in a myriad of configurations to contain absorbent articles. For example, the package may comprise a plurality of panels which define an interior compartment and enclose one or more than one absorbent article. When in a sealed state, such as during transport and on display on a store shelf, the package may completely enclose the one or more than one absorbent article. Each of the panels comprises an inner surface—facing inward toward the packaged absorbent article—and an outer surface—facing outward toward the consumer. The outer surface and/or inner surface of one or more panels may comprise inks or dyes which create branding on the package, package information, and/or background color. The branding and/or package information associated with the absorbent articles within the package may be provided on an outer surface of at least one panel. Branding may include logos, trade names, trademarks, icons, and the like, associated with the absorbent articles within the package. Branding may be utilized to inform a consumer of the brand of the absorbent articles within the package. As an example, branding for a package of feminine hygiene pads may comprise the brand name Always®. Package information may include the size of the absorbent articles, the number of absorbent articles within the package, an exemplary image of the absorbent articles contained within the package, recyclability logos, and the like. As an example, package information for a package of feminine hygiene pads may comprise a size indicator, e.g., "Size 1."

The package materials of the present disclosure may be supplied by a manufacturer of package materials to an absorbent article manufacturer. The package materials may be pre-formed to some extent into a finished package shape, or the manufacturer of package materials may simply provide rolls of the package materials to the absorbent article manufacturer. The package material may be unitary, meaning that a package is formed from a single piece of package material. For example, multiple folds and seams may be utilized to form the plurality of panels of the package from a single piece of package material. In such examples, the absorbent article manufacturer may create the folds and seams as described herein to form a package for absorbent articles. The packages of the present disclosure may comprise package material which comprises a plurality of discrete portions. Such configurations are described in additional detail herein.

Figure 1B:
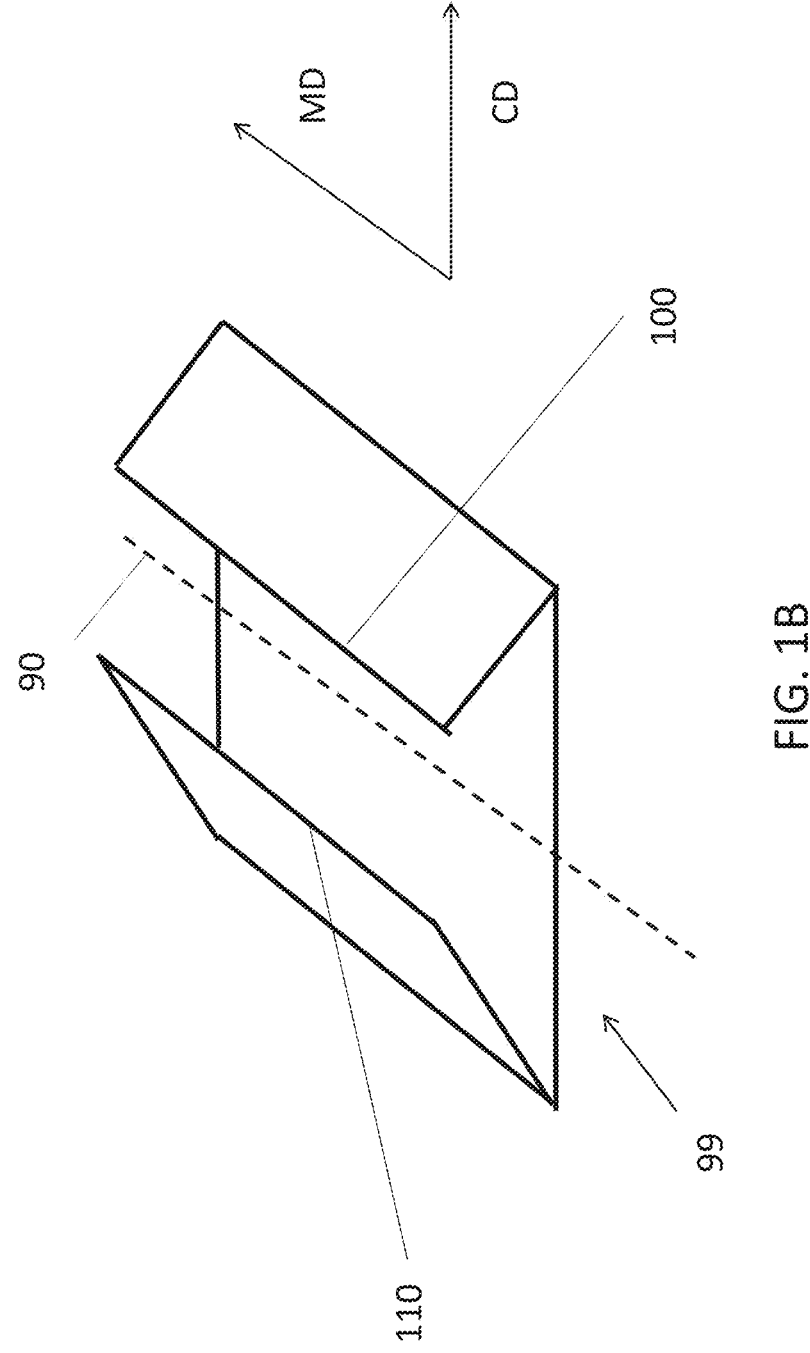
FIG. 1B is a schematic representation showing the package material sheet of FIG. 1A in a partially folded configuration.

Regardless of whether the package material is on rolls or pre-formed to some extent, the packages of the present disclosure begin with paper stock. Referring to FIGS. 1A-1B, edge portions 100 and 110 of a paper stock sheet 99 may be folded towards each other and subsequently sealed to form a seam. For example, side portions 100 and 110 of the sheet 99 may be brought inward towards a longitudinal centerline 90 of the sheet 99 to form a hoop seam 95 (see FIG. 1C). These edge portions may be overlapped with one another and sealed together to form an overlap seam. Alternatively, the edge portions 100 and 110 may be joined together on their respective inner surfaces to form a butt seam. Butt seams tend to not lay as flat as an overlap seam. Therefore, where the seam is located, at least in part, on a bottom panel upon which the package may rest, an overlap seam may be desirable such that the package may sit on a flatter bottom panel.

Figure 1C:
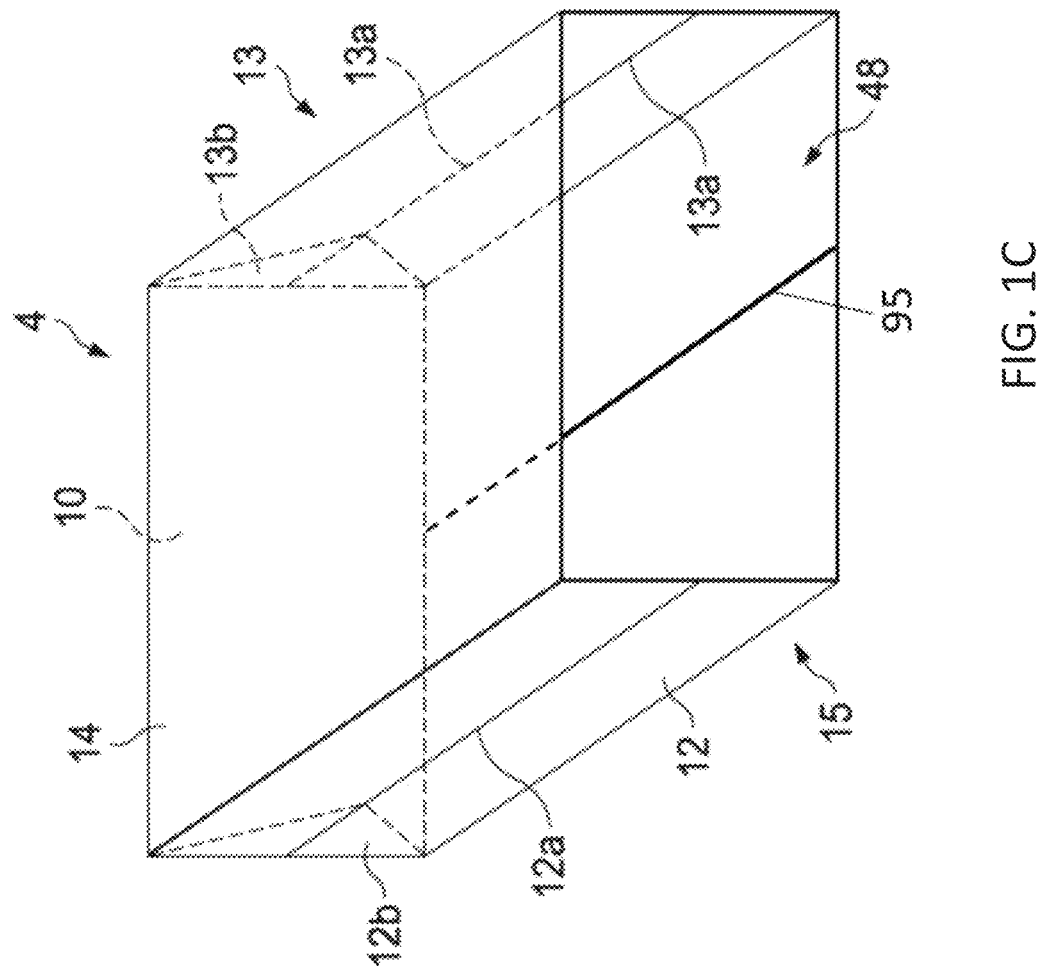
FIG. 1C is a schematic representation of a package with an open end.
Figure 1D:
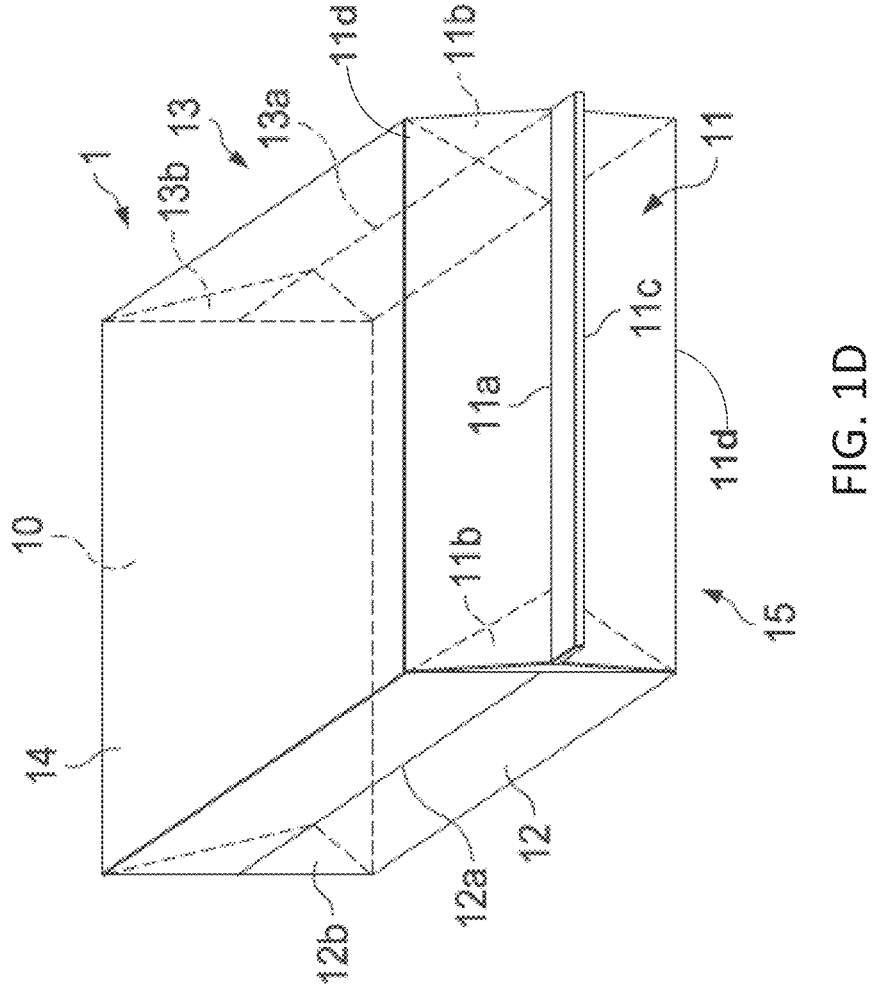
FIG. 1D is a schematic representation of the package of FIG. 1C in a closed state.
Figure 1E:
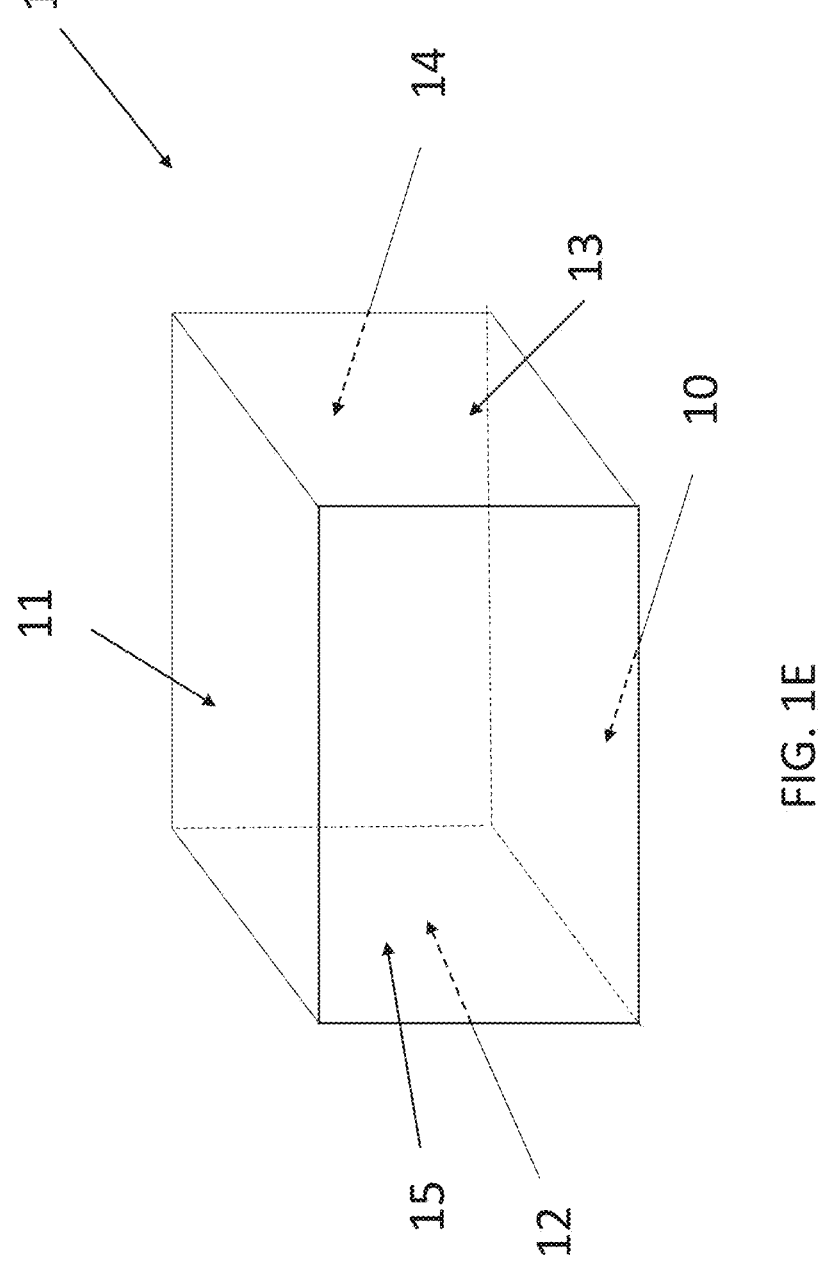
FIG. 1E is a schematic representation of another package of the present disclosure shown in a closed state.

Referring to FIG. 1C-1E, the sheet of packaging material may be suitably folded to form bag side creases 12b and 13b and two side folds 12a and 13a on opposite sides, to form the bag structure 4 having a first surface 10, a second and third surface 12, 13, respectively, and a fourth and a fifth surface 14, 15. An open end 48 opposes the first surface 10. Each side crease 12b, 13b may be located at the respective second or third surface 12, 13. It is worth noting that in FIGS. 1C and 1D, the crease and folds shown are for a package having a block configuration or block bottom configuration. Gussets and fold lines for a pinch bottom bag are discussed in additional detail with regard to FIG. 2B.

The bag 4 may be filled by inserting articles, such as a plurality of absorbent articles, through the open end 48. When the bag 4 is filled with a plurality of articles, e.g., by loading articles from the open end 48, the device used to introduce the articles inside the bag 4 together with the articles may exert some tension on each of the second and third surfaces 12, 13 of the bag 4. For example, the articles may be compressed before being inserted into the bag 4 so that the articles may slightly expand after they are introduced in the bag 4, and thus exert some tension on the second and third surfaces 12, 13 as well as the fourth surface 14 and the fifth surface 15. The tension may be exerted on each of the creases 12b, 13b at the respective second and third surfaces 12, 13, particularly along the first and second side folds 12a, 13a by which the package may maintain a substantially parallelepiped shape.

As may be appreciated from FIG. 1D, the open end 48 opposite the first surface 10 may then be closed to form a sixth surface 11. Any suitable style of closing may be utilized. In a form, the sixth surface may comprise closing gussets 11b, wherein portions of the outer surface of the package material at the closing gussets 11b are brought to form a closing seam 11a and a closing seam fin 11c extending from the closing seam 11a, and sixth surface 11. At least a portion of the closing seam fin 11c may be attached to at least a portion of the sixth surface 11. Tacking down the closing seam fin 11c to at least a portion of the sixth surface may reduce the risk of unintentional opening of the package, provide for increased stackability, as well provide a cleaner look on-shelf look. Instead of forming closing gussets and a closing fin, the sixth surface may comprise seams which are joined together in a block style configuration or cross style configuration, discussed further herein.

Figure 2A:
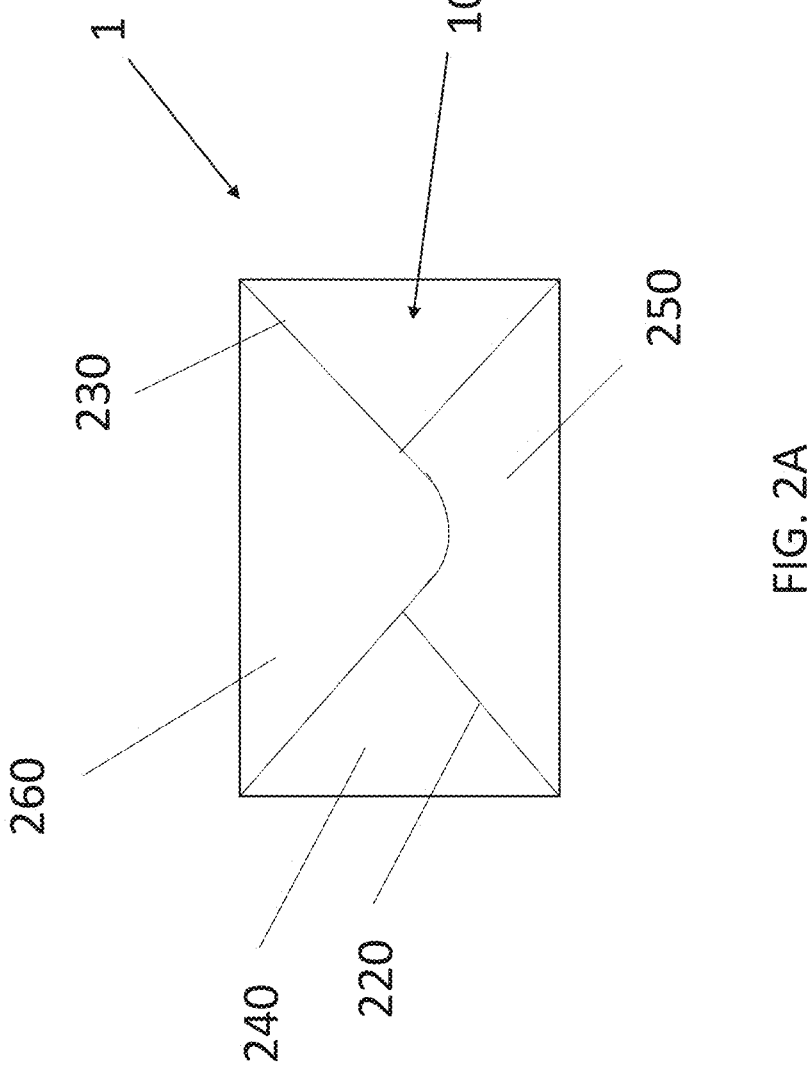
FIG. 2A is a schematic representation showing a panel of a package of the present disclosure, wherein the panel comprises seals in a block bottom configuration.

An example of a block style configuration is shown in FIG. 2A. As shown, the first surface 10 may comprise block style seams 220 and 230. The first surface 10 may comprise a base portion 240. A first flap of package material 250 may be folded onto the base portion 240. First seams 220 may be provided to attach the first flap of package material 250 to the base portion 240. A second flap of package material 260 may be folded onto the base portion 240 and on top of the first flap of package material 250. Second seams 230 may be provided to attach the second flap of package material 260 to the base portion 240 and to the first flap of package material 250. A similar execution may be utilized regarding the sixth surface 11 to form a closure.

Figure 2B:
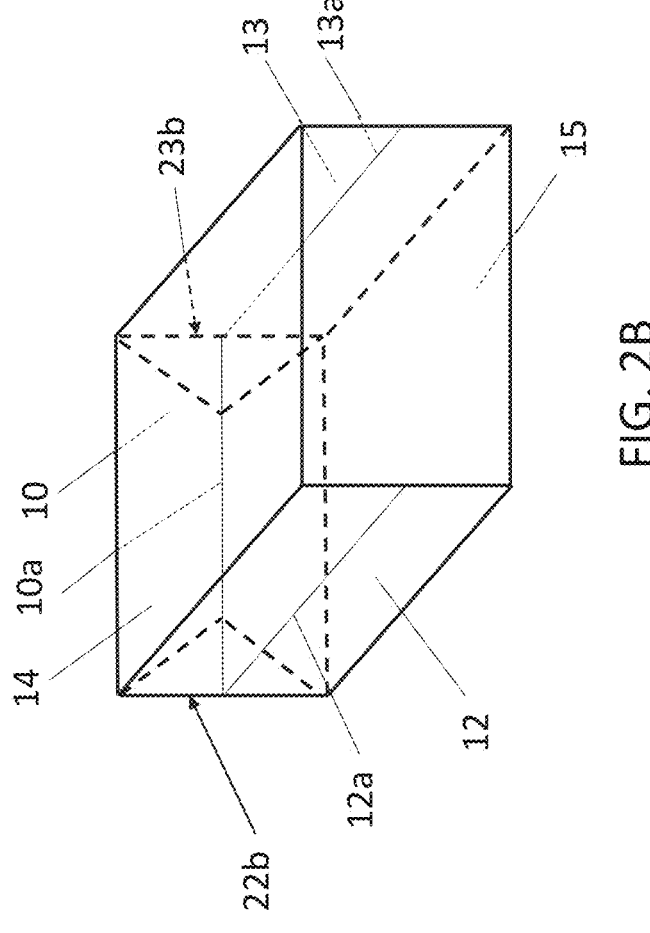
FIG. 2B is a schematic representation showing a panel of a package of the present disclosure, wherein the panel comprises seals in a pinch bottom configuration.

Another example of a panel sealing style which may be utilized with the packages of the present disclosure is the pinch style configuration or the pinch bottom style. An example of a pinch style configuration is shown in FIG. 2B. As shown, one of the key differences between the block bottom and the pinch bottom configuration is the configuration of the creases 12b and 13b. Instead of creases on the sides 12 and 13, a pinch style configuration comprises gussets 22b and 23b on the first surface 10. Additionally, in the pinch bottom configuration, the first surface 10 comprises a fold line 10a which may be absent in the block style configuration. A similar pinch style configuration may be utilized regarding the sixth surface 11 to form a closure.

Figure 2C:
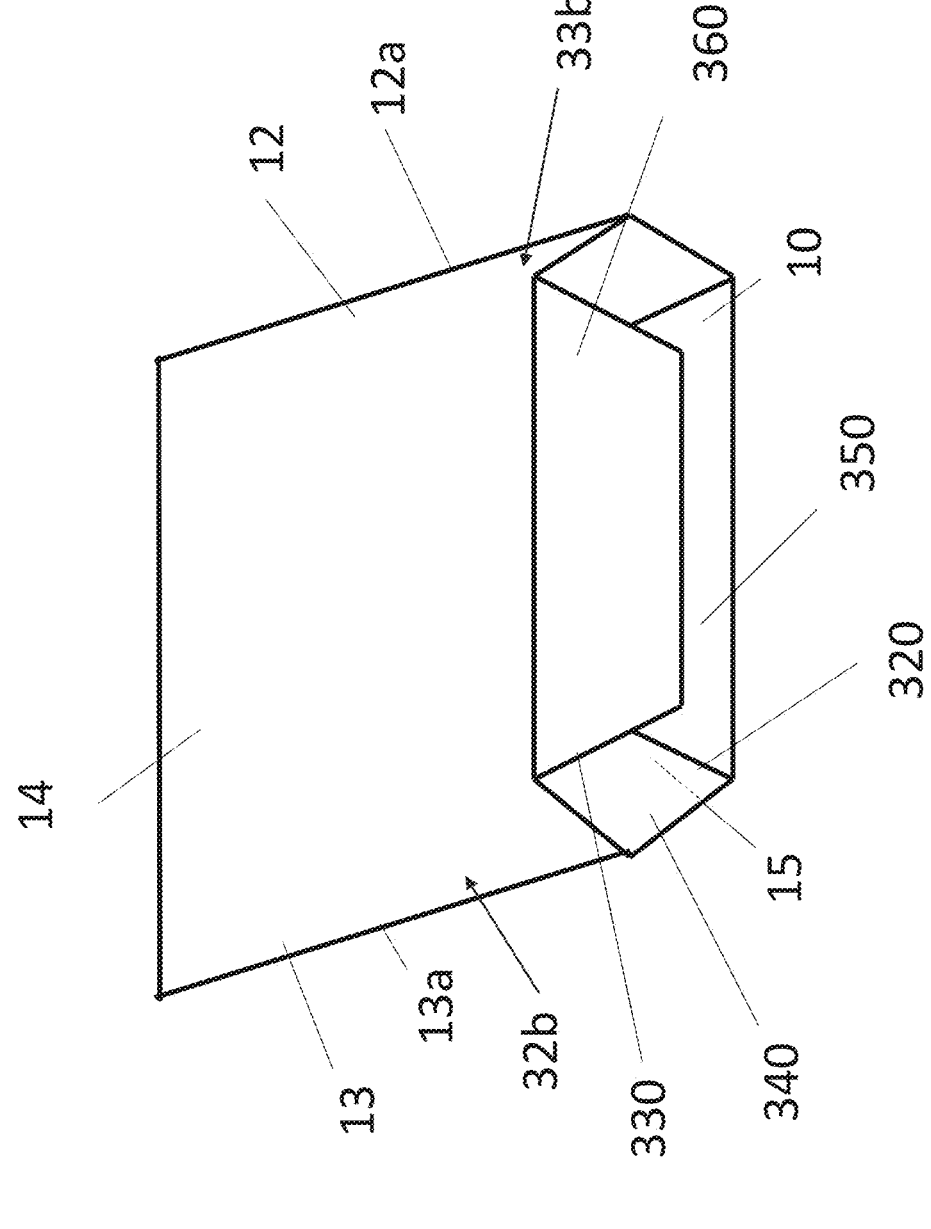
FIG. 2C is a schematic representation showing a panel of a package of the present disclosure, wherein the panel comprises seals in a cross bottom configuration.

Cross style or cross bottom style configurations are also acceptable for sealing portions of the package materials of the present disclosure. An example of a cross style configuration is shown in FIG. 2C. As shown, one of the key differences between the cross style configuration and the block style configuration is that gussets 32b and 33b and fold lines 12a and 13a are oriented outward of the interior of the package. In a block-style configuration (FIG. 1C), on the other hand, fold lines 12a and 13a on the second surface 12 and the third surface 13, respectively, are oriented inward prior to filling the package. Due to the orientation of the gussets 32b and 33b in the cross style configuration, filling the package with absorbent articles may require less energy to expand the package for filling. As an example, creases oriented inward, e.g., block style configuration, would require displacement outward of the creases prior to filling the package. Additionally, the equipment utilized in guiding the product into the package may have a reduced likelihood of interfering with the gussets, given their orientation outward. This may reduce the likelihood of packaging mishaps or manufacturing process stoppages due to quality issues.

Referring again to FIG. 2C, similar to the block style configuration, the first surface 10 of the cross style configuration comprises seams 320 and 330. The first surface comprises a base portion 340. A first flap of package material 350 may be folded onto the base portion 340. First seams 320 may be provided to attach the first flap of package material 350 to the base portion 340. A second flap of package material 360 may be folded onto the base portion 340 and on top of the first flap of package material 350. Second seams 330 may be provided to attach the second flap of package material 360 to the base portion 340 and/or to the first flap of package material 350. A similar execution may be utilized to form the closure on the sixth surface (formed once the package is sealed after the placement of absorbent articles therein).

For less bulky items, where standability of the package is desired, the block bottom or cross bottom may be desirable, as these configurations form a flat base. However, for bulky items, the pinch style configuration bags may be beneficial as the bulky absorbent articles therein may form a steady base for the package to stand. The inventors have surprisingly found that diapers may be suited for pinch bottom bags due their bulky nature. In contrast, feminine hygiene articles, particularly menstrual pads, may be suited for block bottom configured packages.

Additionally, it is worth noting that block style and cross style configured packages tend to be themselves bulkier than their pinch style counterparts. For the purposes of packaging absorbent articles, unfilled packages may arrive pre-formed in stacks to an absorbent article manufacturer. Typically, stacks of pre-formed block style and cross style configuration packages will take up more space—due to their bulkiness—as compared to pre-formed pinch style packages. The bulkiness of the block and cross style configurations may make the stacks more difficult to manipulate during the filling process, particularly where a large number of filled packages are created per minute. In such instances, the bulkiness of these configurations may mean an increased frequency of replenishment of the stacks.

Referring back to FIGS. 1C-1D, the first surface 10 may form at least a portion of the top panel of the package 1. In another embodiment, the first surface 10 may form at least a portion of the bottom panel of the package 1. It is worth noting that if the first surface 10 comprises seams, it may be desirable that the first surface 10 forms at least a portion of the bottom panel. In this way the seams may be hidden from view on the store shelf. The second and third surfaces 12 and 13, as they may comprise gussets 12*b* and 13*b*, respectively, may form at least a portion of a first side panel and opposite second side panel, respectively, or vice versa. The fourth and fifth surfaces 14, 15 may form at least a portion of a front panel and an opposite back panel, respectively, or vice versa. At least one of the fourth and/or fifth surface 14, 15, may comprise branding, product information and/or background color as described herein, as the front panel is generally the consumer-facing panel. However, product information and/or background color may not be limited to the consumer-facing panel. Any combination of the panels of the packages of the present disclosure may comprise branding, product information, and/or background color. The sixth surface 11 may form at least a portion of the top panel or at least a portion of the bottom panel of the package 1. Where the sixth surface 11 comprises closing gussets 11*b*, closing seam 11*a*, and a closing seam fin 11*c* extending from the closing seam 11*a*, it may be desirable that the sixth surface 11 forms at least a portion of the top panel. In this way the closing gussets 11*b* and closing seam fin 11*c* do not introduce bulk and instability to the base of the package. Where the sixth surface 11 forms at least a portion of the top panel, a top edge region 11*d* is formed at the transition from the top panel to the front, back, and first and second side panels. The top edge region 11*d* may be formed by portions of the top, front, back, first side, and second side panels that are adjacent to a fold in the package material designating a transition from the top panel to another panel.

The closing seam fin 11*c* may comprise a carrying handle 1200, as shown in FIGS. 6, 12A-16, and 18A. The carrying handle 1200 may be formed by a portion of the closing seam fin 11*c* that is devoid of packaging material. In a form, as least a portion of the packaging material forming the closing seam fin 11*c* may be excised to define the carrying handle 1200. The carrying handle 1200 may be configured to allow a user to engage the carrying handle 1200 without needing to grasp the handle with the user's hands. For example, the carrying handle 1200 may be sized to allow a user to slip their entire hand through the carrying handle 1200, and hook the carrying handle 1200 around the user's wrist, thus keeping the user's hand free. As such, the area defining the carrying handle 1200 may measure at least 100 cm², at least 150 cm², at least 200 cm², or at least 250 cm².

Figure 17:
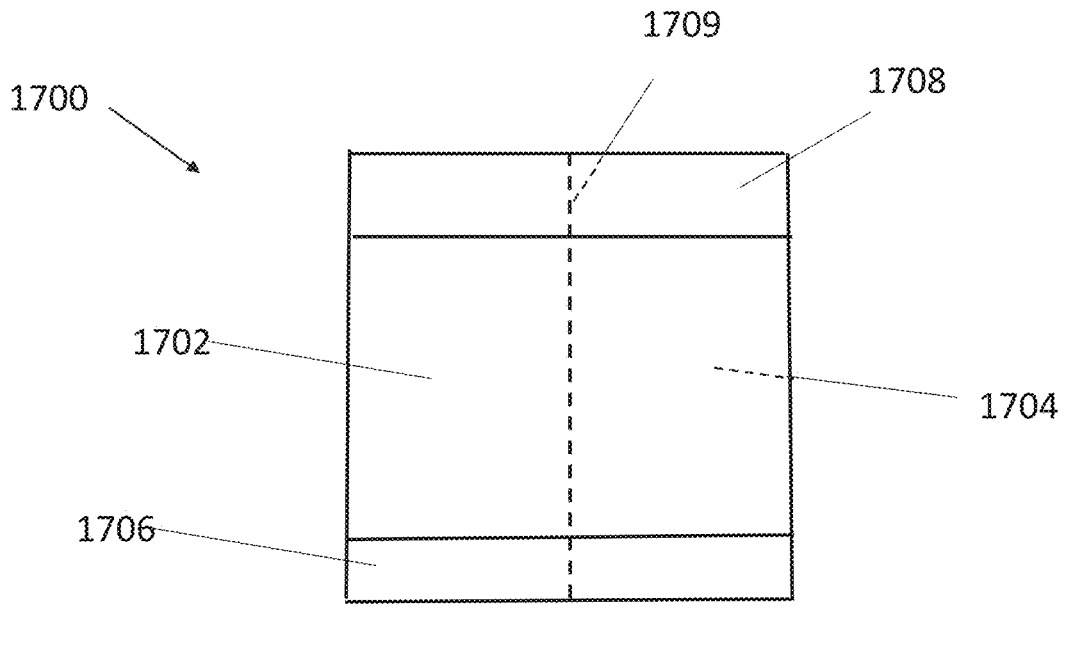
FIG. 17 is a schematic plan view of a package of the present disclosure constructed with a flow wrap process.
Figures 18A, 18B:
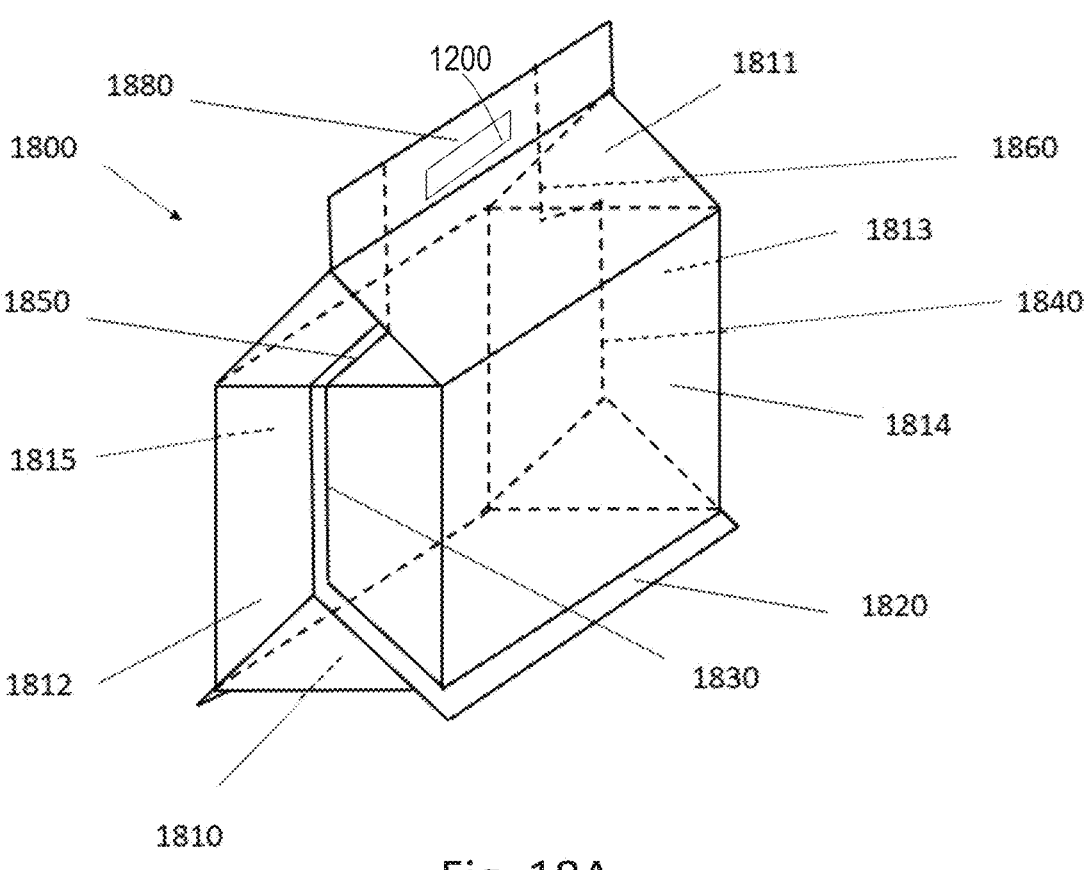
FIG. 18A is a schematic representation of a package configuration in accordance with the present disclosure constructed in accordance with the present disclosure.
FIG. 18B is a schematic representation of a front view of the package configuration of FIG. 18A.

Other package shapes are contemplated. Examples of such packages include flow wrap or horizontal form fill-and-seal wrap. Such packages may comprise a generally cuboid shape also configured as described above. However, in some instances, such as shown in FIG. 17, a flow wrap package 1700 may comprise a first surface 1702 and an opposing second surface 1704. Rounded edges may be provided as a transition between the first surface 1702 and the second surface 1704. In another form, one or more fold lines may be provided between the first surface 1702 and the second surface 1704. The flow wrap package 1700 may further comprise end seals 1706 and 1708, and a hoop seam 1709 which may be disposed on the second surface 1704. In such packages, the first surface 1702 may comprise the consumer-facing panel. Flow wrap packages may be useful, particularly where a low number of absorbent articles are included within a package.

Another package form in accordance with the present disclosure may comprise seams/seals which are move overt than those packages comprising a block bottom, pinch bottom, and/or cross bottom. Referring to FIG. 18, a package 1800 is shown. The package 1800 may be configured in generally a cuboid shape. The package 1800 may comprise a first panel 1811, opposing second and third panels 1812 and 1813, opposing fourth and fifth panels 1814 and 1815, and a sixth panel 1810 opposing the first panel 1811. As shown, between the fourth panel 1814 and the sixth panel 1810, a first seal 1820 extends outward. The first seal 1820 may form a sort of foot for the package 1800. A second seal (not shown) may extend outward between the fifth panel 1815 and the sixth panel 1810 in a similar fashion to the first seal 1820.

The first seal 1820 can extend such that a portion of the first seal 1820 is on the second panel 1812 and another portion of the first seal 1820 is disposed on the third panel 1813. Similarly, a portion of the second seal may be disposed on the second panel 1812 and another portion may be disposed on the third panel 1813. The first seal 1820 and the second seal may be provided where the sixth panel 1810 is formed from a discrete piece of material which is subsequently joined to the fourth panel 1814 and fifth panel 1815. Of course, forms where the sixth panel 1810 is unitary with the fourth panel 1814 and fifth panel 1815 are also contemplated.

A third seal 1830 and a fourth seal 1840 may extend outward from the second panel 1812 and the third panel 1813, respectively. It is worth noting that the first seal 1820, second seal, third seal 1830, and fourth seal 1840 collectively may comprise the hoop seal discussed herein. Thus, one, all, or any combination, of these seals may exhibit the tensile strength for the hoop seal as described herein.

As shown, the package 1800 may further comprise a fifth seam 1850 and a sixth seam 1860 which are disposed on the sixth panel 1811. The fifth seam 1850 and sixth seam 1860 can extend into a seal fin 1880. It is worth noting that the package 1800 and the seams associated therewith, may be assembled as described herein regarding adhesives, barrier films, and/or combinations of barrier films and adhesives. However, the construction of the package 1800 is particularly well suited for the creation of seams via barrier film coating on an inner surface of the package material. In such configurations, the film may form a barrier that reduces the likelihood or at least the amount of moisture vapor through the package material to the absorbent articles therein.

Package shapes are also contemplated where the package comprises less than six panels. Packages having a circular or semi-circular shape when viewed from a bottom panel are contemplated. Additionally, packages having a triangular shape when viewed from the bottom panel are contemplated. Regardless of the number of panels comprised by the packages of the present disclosure, the package comprises a consumer-facing panel.

Absorbent Article Configuration

The packages of the present disclosure may comprise one or more absorbent articles. The absorbent articles may be placed into the package in an unfolded or folded configuration. The articles may be folded laterally and/or longitudinally. The articles may comprise one fold line, and may be disposed within the package in a bi-fold configuration. The articles may comprise two fold lines, and may be disposed within the package in a tri-fold configuration.

Figures 3A, 3B:
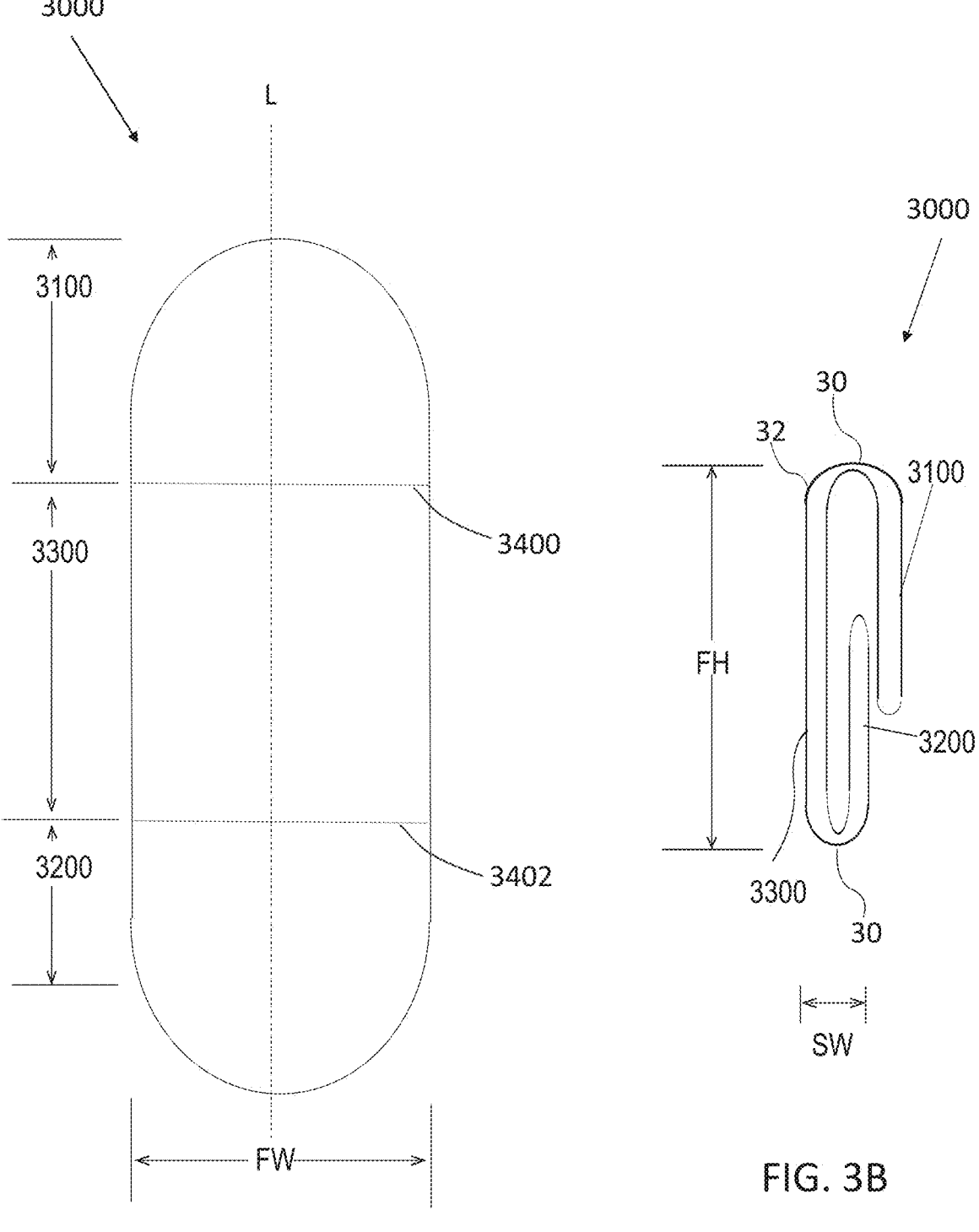
FIG. 3A is a plan view of an example of an absorbent article in the form of a feminine hygiene pad in an unfolded configuration.
FIG. 3B is an edge side view of the feminine hygiene pad of FIG. 3A, shown folded about lateral fold lines in a tri-fold configuration.

FIG. 3A depicts an example of a feminine hygiene pad in an unfolded configuration. FIG. 3B depicts a side view of the feminine hygiene pad of FIG. 3A in a tri-fold configuration. The feminine hygiene pad depicted in FIGS. 3A and 3B comprises a first fold line 3400 disposed between a first end region of the pad 3100 and a central region of the pad 3300, and a second fold line 3402 disposed between a second end region of the pad 3200 and the central region 3300. Prior to placement within the package, the second end region 3200 may be folded over and longitudinally inward about the second fold line 3402 to overlap at least a portion of the central region 3300, as may be appreciated from a comparison of FIGS. 3A and 3B. The first end region 3100 may then be folded over and longitudinally inward about the first fold line 3400 to overlap at least a portion of the central region 3300 and a portion of the second end region 3200. In some examples a tri-fold configuration may have the article folded approximately in thirds, about the two longitudinally-spaced lateral fold lines.

Figure 4A:
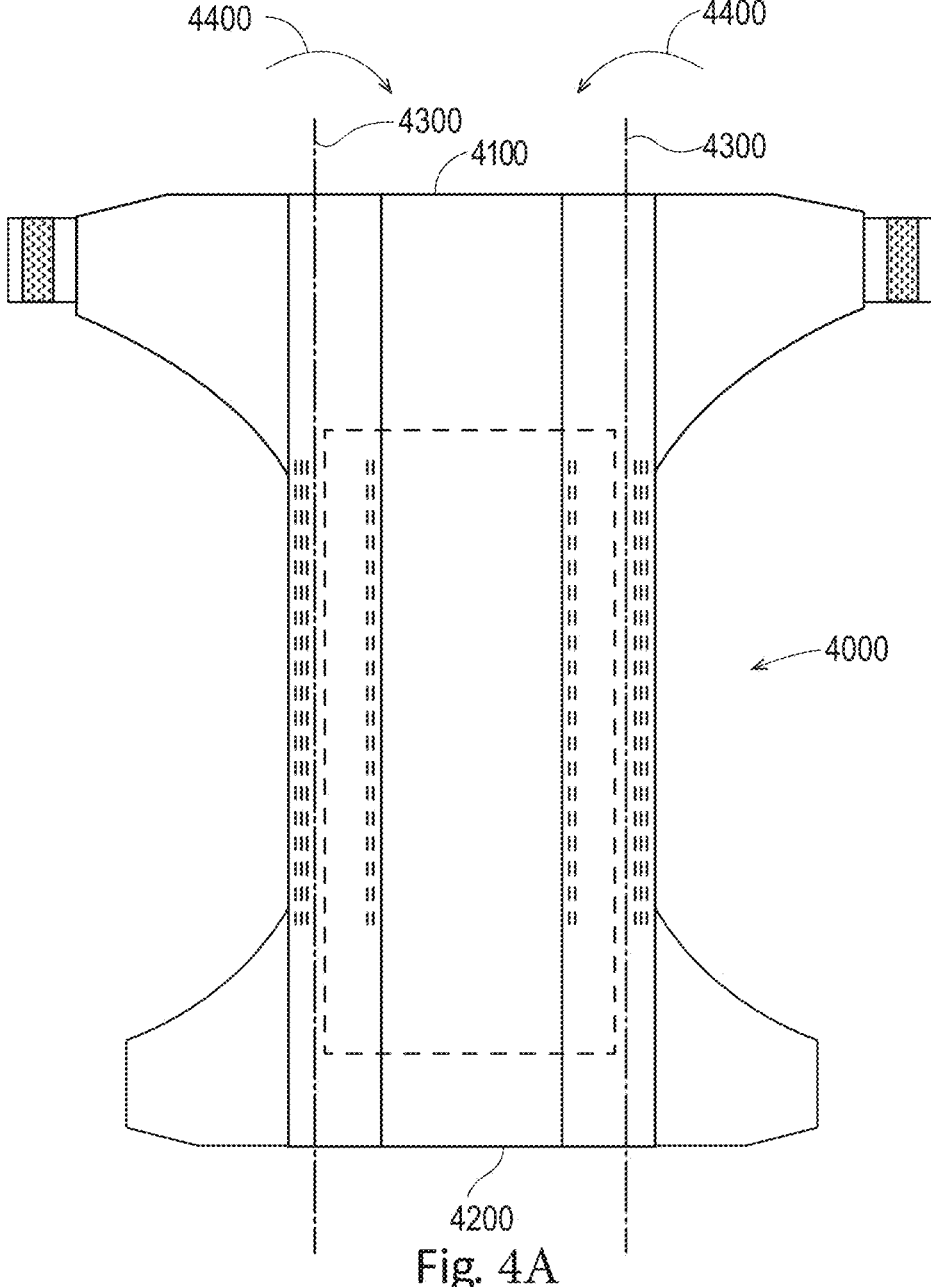
FIG. 4A is a plan view of an example of an absorbent article in the form of a disposable diaper, wearer-facing surfaces facing the viewer.
Figure 4B:
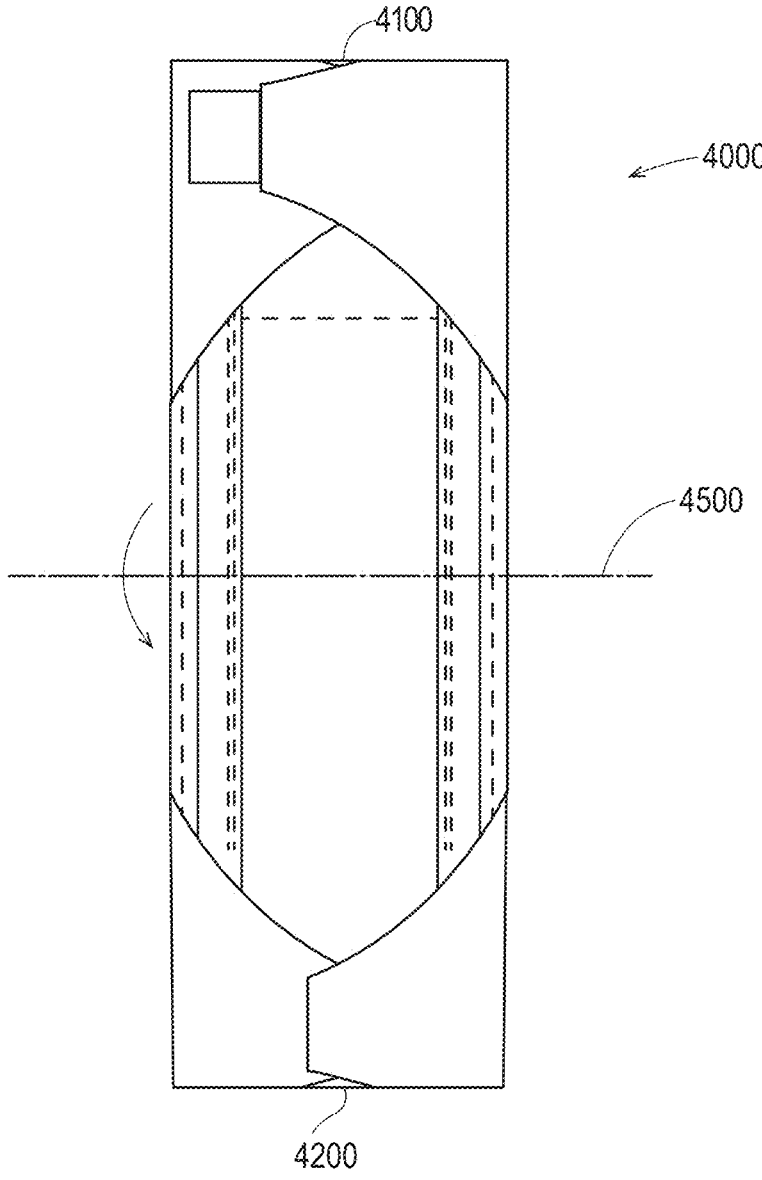
FIG. 4B is a plan view of the diaper of FIG. 4A, shown with side portions folded over and laterally inward about longitudinal side edge fold lines.

FIGS. 4A-4D depict an absorbent article in the form of a diaper 4000 with front and rear waist edges 4100, 4200, in successively open/unfolded and folded configurations. For packaging in bulk, each of a plurality of diapers such as that shown in FIG. 4A may, in a possible first step, have its longitudinal side portions be folded over and laterally inward about longitudinal side edge fold lines 4300, as may be appreciated from a comparison of FIGS. 4A and 4B. Next, the diaper may, in a second step, be folded longitudinally, about lateral fold line 4400 that passes through the crotch region of the diaper, as may be appreciated from a comparison of FIGS. 4B and 4C. For a bi-fold configuration such as depicted in FIGS. 4C and 4D, the article may be folded longitudinally once, and may in some examples be folded approximately in half about the lateral fold line 4400.

Regardless of whether the article is in a bi-fold or tri-fold configuration, the folded article, such as folded feminine hygiene pad 3000 and/or folded diaper 4000, may have a single fold nose 30 defining at least one end edge of the folded article, fold nose corners 32, and left and right longitudinal peripheral edges 4500, 4600. It will be appreciated that in a tri-fold example, a single fold nose may define each of both end edges of the folded article. In some examples, such as depicted in FIGS. 4C and 4D, fold nose 30 may be proximate the crotch region of the article (the middle region of the article adapted to be located between the wearer's legs during wear). The folded article will have a folded width FW measured as the distance between side edges, a folded height FH measured as the distance between fold nose 30 and the end edges (in the case of a bi-fold configuration) or between the two fold noses 30 (in the case of a tri-fold configuration), and a side width (SW). The folded width (FW) forms the flat, broad face of the folded absorbent article, while the side width (SW) forms the narrow folded side of the absorbent article.

Figure 5:
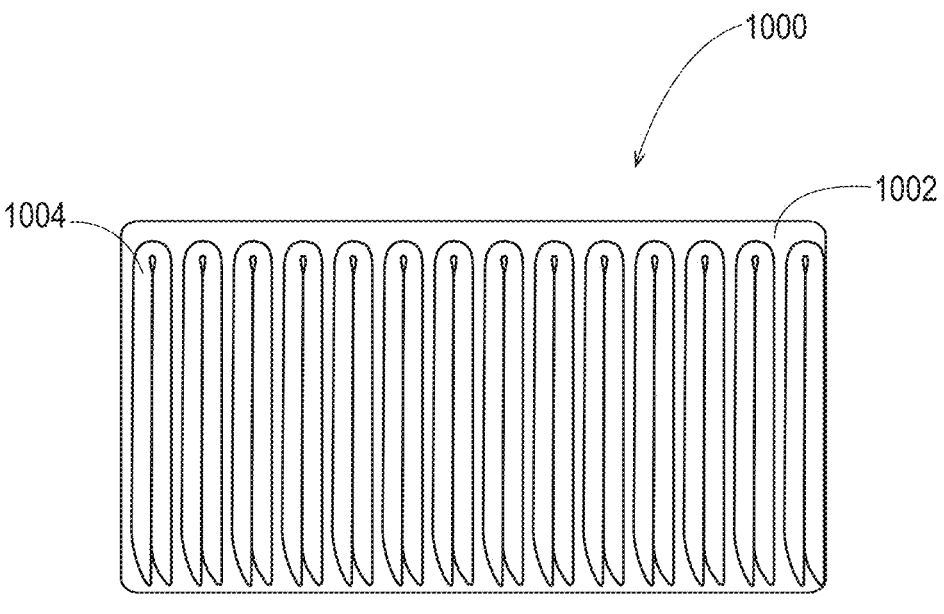
FIG. 5 is a side view of a stack of a plurality of absorbent articles disposed within a package of the present disclosure.
Figure 6:
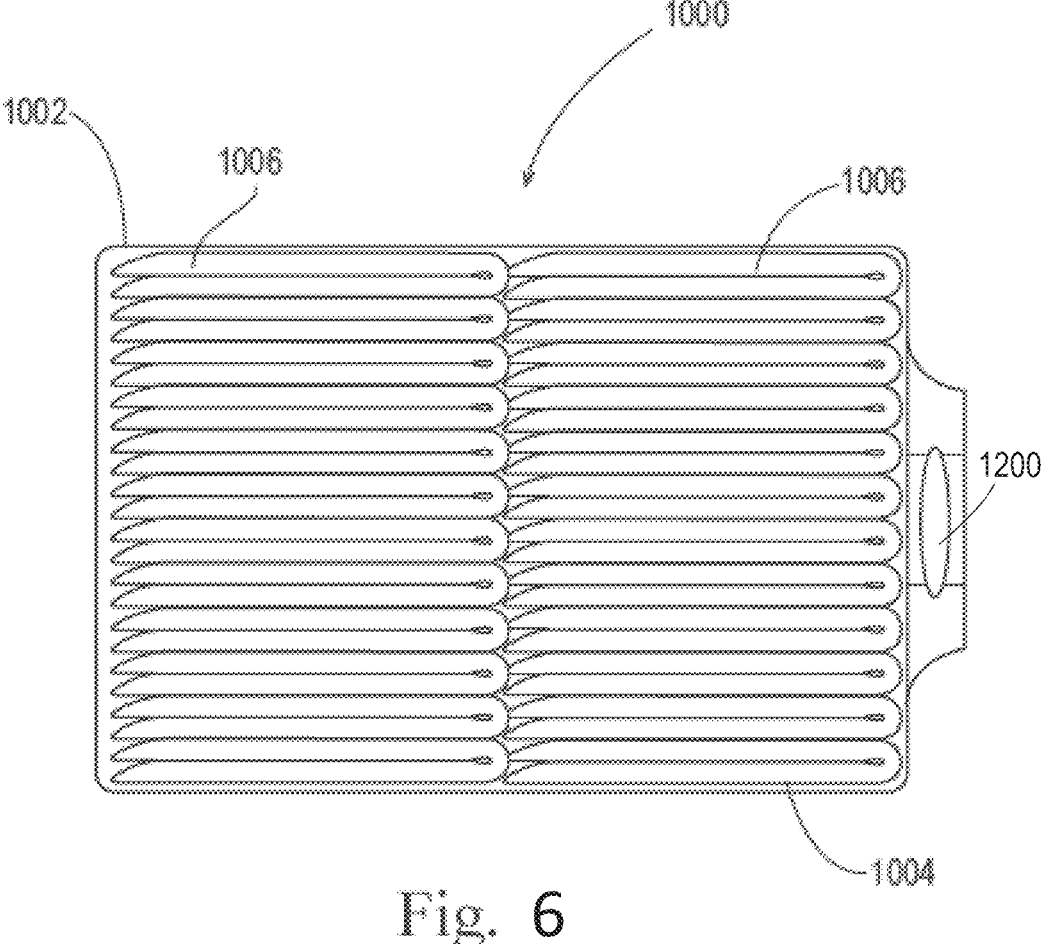
FIG. 6 is a front view of a multiple stacks of a plurality of absorbent articles disposed within a package of the present disclosure.

A plurality of folded articles such as depicted in FIGS. 3B and 4C and 4D may be placed in similar orientation within the interior compartment of a package of the present disclosure. FIGS. 5 and 6 depict a plurality of absorbent articles disposed within a package of the present disclosure. As shown in FIGS. 5 and 6, the package 1000 defines an interior compartment 1002 in which a plurality of absorbent articles 1004 are situated. The plurality of absorbent articles 1004 may be arranged in a single horizontal row, as shown in FIG. 5, or in one or more vertical stacks 1006, as shown in FIG. 6. Where the articles are arranged in more than one vertical stack, as shown in FIG. 6, all the articles may be oriented in the same direction. In another example, a first set of the plurality of folded articles may have their fold noses 30 oriented along one side of the stack, and a second set of the plurality of folded articles may be rotated 180 degrees to have their fold noses oriented along the opposite side of the stack. In some examples, the articles in the first set and the articles in the second set may appear in alternating sequence in the stack.

The folded absorbent articles may be disposed within the package of the present disclosure such that the folded width (FW) faces toward the first and second side panels. Such a configuration may be employed where the number of absorbent articles within the package is relatively large, e.g., greater than about ten individual absorbent articles, because the narrower sides (SW) of the articles will form front and back panels. Therefore, a relatively large number of absorbent articles may then be utilized to build up the front and back panels of the package. Such a configuration may be beneficial where the front and/or back panels form the consumer-facing panel.

The folded absorbent articles may be disposed within the package of the present disclosure such that the folded width (FW) faces toward the front and back panels. Such a configuration may be employed where the number of absorbent articles within the package is relatively low, e.g., less than about ten individual absorbent articles, because the wider sides (FW) of the articles will form front and back panels. Such a configuration may be beneficial where the front and/or back panels form the consumer-facing panel, and the number of absorbent articles disposed within the package is less than about ten.

The absorbent articles or articles may be packed under compression so as to reduce the size of the package, while still providing an adequate number of absorbent articles per package. By packaging the absorbent articles under compression, caregivers can easily handle and store the packages, while also providing distribution savings to manufacturers owing to the reduced size of the packages. Despite lacking the stretch properties of conventional plastic packaging material, the inventors have surprisingly found the package materials of the present disclosure are able to withstand the processing and distribution rigors, as mentioned herein, even with absorbent articles which are compressed within the package and without the use of an intermediate container. This is particularly unexpected as the materials of the present disclosure may not display the stretch properties of presently used conventional plastic films.

Packages of absorbent articles of the present disclosure may have an In-Bag Stack Height of less than about 150 mm, less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 150 mm, from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test Method described herein.

Opening Features

The packages of the present disclosure containing absorbent articles comprise features that facilitate opening without unwanted deformation or destruction of the package (opening features), so that the opened packaged may be used, following opening, as a container to store the supply of unused product. The opening features comprise a weakened region or a plurality of weakened regions. The inventors have surprisingly found that packages of the present disclosure having a balance between the strength properties of the package materials and the strength properties of the weakened region may provide a flexible and resilient package that may withstand the rigors of a manufacturing process while also providing for an opening feature that is configured for ease of package opening and minimized strain of the package material along the path during opening. The packages of the present disclosure may also retain their shape upon removal of absorbent articles, which may make extraction of further articles easier.

The weakened regions may have a tensile strength that is less than the tensile strength of unweakened regions of the packages to allow for the package to be opened at the weakened regions, while the unweakened regions of the package remain intact. The tensile strength of the weakened regions may, however, be sufficient to withstand unintentional opening during package formation, shipment, store display, and daily use by a consumer.

The inventors have also found that formation of weakened regions may be more efficient and less cumbersome where the packages are formed from a single layer (one ply) of package materials as opposed to multiple layers. As discussed herein, the package materials of the present disclosure may allow for the formation of packages comprising a single layer of package material while exhibiting sufficient strength and resilience. Disposition of weakened regions in a single layer (one ply) of package materials may require less energy and time as compared to disposition of weakened regions through multiple layers of material.

Weakened regions may comprise folds disposed in the package material configured to render the weakened region less resistant to tearing or bursting than unfolded portions of the package material. Weakened regions may also, or instead, comprise perforations and/or scoring in the package material. Perforations and/or scoring may form a path or paths along a portion or portions of the package material. The path may be continuous. For purposes herein, a "continuous" path of perforations or scoring is a singular path of individual, successive, mechanically-created partial or complete perforations, a singular path of individual, successive laser-scored partial or complete perforations, or a continuous, singular path of mechanical and/or laser scoring, that is uninterrupted by an unperforated/unscored portion of the package material. The packages of the present disclosure may comprise a single path or may comprise multiple paths of perforations and/or scoring. The path or paths of perforations and/or scoring may form a generally straight line, or may form a curvilinear shape.

As shown in the non-limiting examples of FIGS. 7A-7E, individual perforations and/or scoring defining a path 60 may have any configuration suitable for propagating a tear in the package material along the path. Where the path 60 of perforations and/or scoring comprises a plurality of individual mechanically-created perforations or cuts, or individual laser-scored perforations or cuts, it may be desired that the path have a cut-to-land ratio of between about 0.7:1 and about 6:1, between about 0.8:1 and about 5:1, or between about 1:1 and about 4:1, specifically reciting all values within these ranges and any ranges formed therein or thereby. For package materials of the type contemplated herein, it is believed that a cut-to-land ratio within this range strikes a suitable balance between providing for ease of package opening and minimized strain of the package material along the path during opening, and avoiding premature, unintended package bursting or opening, and retaining structural integrity of the package during formation, shipping, handling, and other events prior to intentional opening by the consumer. For purposes herein, the "cut-to-land ratio" of a path of perforations and/or scoring is the ratio of the aggregate of the lengths of the perforations or cuts extending along the path direction, to the aggregate of the minimum distances of unperforated/unscored portions of the package material between successive perforations. Referring to FIG. 8, for example, in which a portion of a path of successive diagonally-tilted rectangular perforations is depicted lying along path direction PD, the cut-to-land ratio is (L1+L2+ L3):(D1+D2+D3).

Figures 7A, 7B, 7C, 7D, 7E:
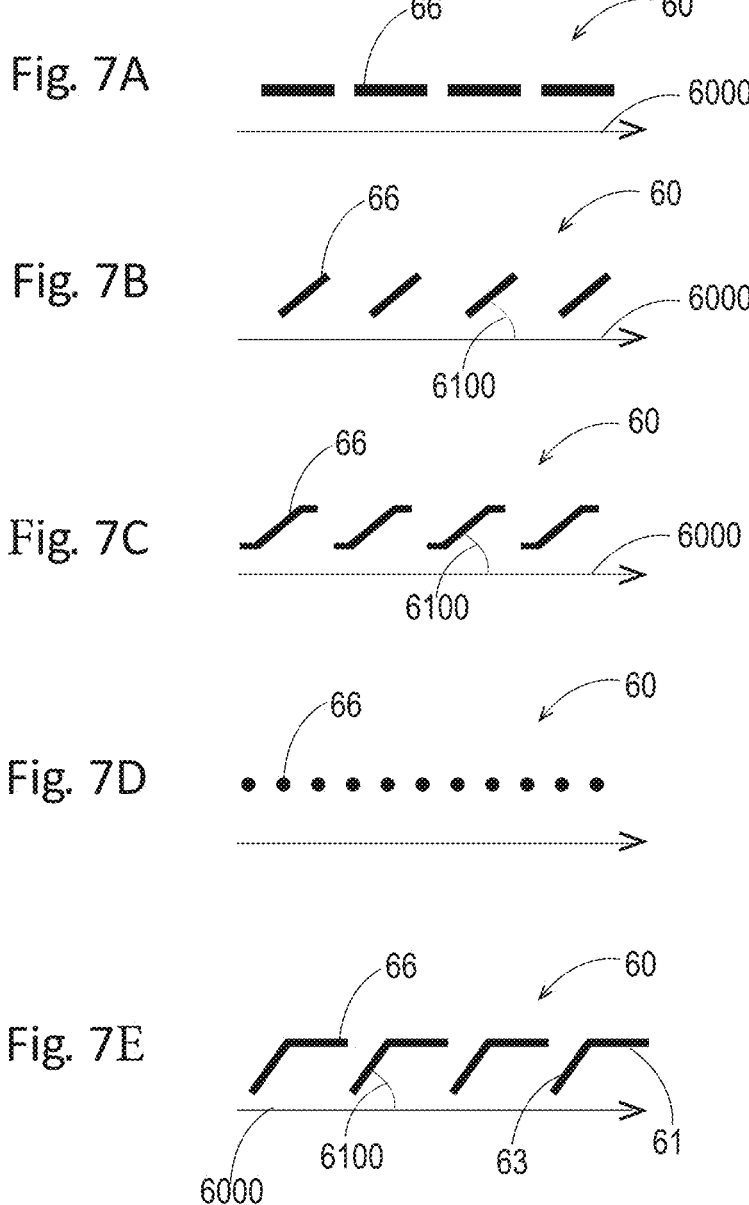
FIGS. 7A-7E are schematic plan view depictions of examples of configurations of perforations.

The individual perforations and/or scoring may comprise any configuration capable of forming a weakened region. As shown in FIG. 7A, the individual perforations and/or scoring 66 may be in the shape of a straight line. The straight line perforation and/or scoring, as shown in FIG. 7A, may be aligned generally parallel with the path 60 of perforations and/or scoring. As shown in FIG. 7B, the individual perforations and/or scoring 66 may be aligned such that each individual perforation and/or scoring is disposed at an angle to the path 60 of perforations and/or scoring. The angle may be between about 20° and about 80°. Referring to FIG. 7E, the individual perforations and/or scoring 66 may comprise a first leg 61 and a second leg 63. The first leg 61 may be disposed generally parallel to the path 60 of perforations and/or scoring. The second leg 63 may be disposed at an angle to the path 60 of perforations and/or scoring. The angle may be between about 20° and about 80°. In another form, the second leg 63 may be disposed generally parallel to the path 60 of perforations and/or scoring, and the first leg 61 may be disposed at an angle to the path 60 of perforations and/or scoring, wherein the angle may be between about 20° and about 80°. Referring to FIG. 7C, the individual perforations and/or scoring 66 may comprise three legs, wherein at least one of the legs may be disposed at an angle to the path 60 of perforations and/or scoring, and wherein the angle may be between about 20° and about 80°. It is believed that weakened regions comprising perforations and/or scoring comprising at least one leg disposed at an angle to the path of perforations and/or scoring may exhibit lower tensile strength, yet be more resistant to tearing and accidental opening during manufacturing processes.

Referring to FIGS. 9A-9E, where the packages of the present disclosure comprise weakened regions comprising multiple paths of perforations and/or scoring 60, the paths may be separated by registered land areas 62. The registered land areas 62 may have a larger length than the land areas of the paths they separate, when measured in line with adjoining paths. The length of the registered land area may be large enough to distinguish it from the land areas of the adjoining paths of perforations and/or scoring, but may not be so large that it disrupts the opening of the two adjoining paths upon one application of force from a user. The registered land area may be coincident with a fold or crease in the package material, such as at a corner between two panels. The registered land area may help to prevent the unintended opening of the opening features at portions of the packages that may be pre-weakened or that may experience some increased amount of stress due to weakened region's disposition on a fold and/or crease in the package. Registered land areas may have a length of between about 1.5 mm and about 25 mm, from about 2 mm to about 20 mm, or from about 2 mm and about 10 mm, specifically reciting all 0.1 mm increments within the specified ranges and all ranges formed therein or thereby.

The path of perforations and/or scoring may comprise a single, uninterrupted line of laser scoring that does not entirely penetrate the package material, but is configured to promote neat tear propagation along the path. The uninterrupted line of laser scoring may be disposed on the package material coincident with a fold line, or may be disposed on a flat portion of the package material. Disposal of a single, uninterrupted line of laser scoring coincident with a fold line may enhance the ability of an already weakened region to tear or burst along a designated path upon application of sufficient force, while the rest of the package retains its shape and integrity.

Referring again to FIGS. 7A-7E, the configuration of the perforations in the path 60 of perforations may depend on the location on the package where the weakened region is disposed. Configurations of perforations having a higher cut-to-land ratio may be desirable in a weakened region which comprises a path of perforations traverses a gusset structure, because a gusset structure includes more than one layer of package material and may be more difficult to tear. Additionally, where a plurality of absorbent articles are packaged within the package of the present disclosure under compression, the configuration of perforations may be arranged such that at least a portion of the direction of the cuts are arranged diagonal to or perpendicular to the direction of tension in the package material created by the compression of the absorbent articles, such as shown in FIGS. 9B, 9C, and 9E. In such a configuration, it is believed that the perforations will be less likely to spread and/or open prior to intentional opening by the consumer.

Figure 10:
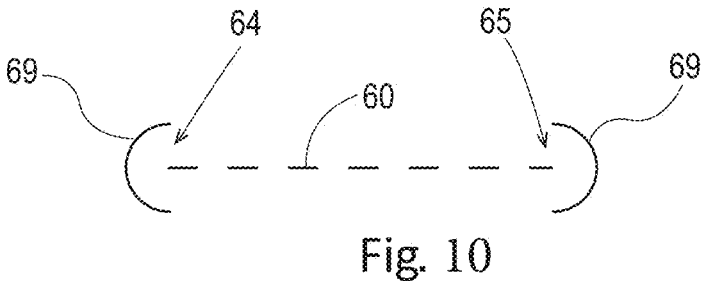
FIG. 10 is a depiction of an endpoint of a path of perforations or scoring, including a tearing stress dispersion feature.
Figure 11:
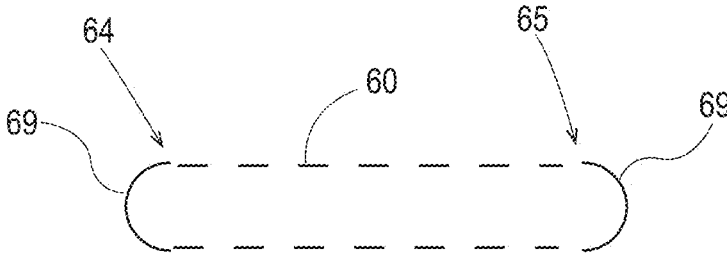
FIG. 11 is a depiction of an endpoint of multiple paths of perforations or scoring, including a tearing stress dispersion feature.

Referring to FIGS. 10 and 11, in order to reduce the chances that a consumer opening the package will tear the package material past endpoints 64, 65 of the path 60 of perforations and/or scoring, and deform the package material and/or reduce the utility of the package for storing and/or protecting unused articles, it may be desired to include a stress dispersion feature 69 proximate one or both endpoints 64, 65. As shown in FIGS. 10 and 11, the tearing stress dispersion feature 69 is a semi-circular perforation or cut running transverse to the direction of the path 60, which serves to disperse tearing stresses concentrated at the endpoint, and obstruct tear propagation in a way that may be perceived tactilely by the consumer. It may be appreciated that tearing stress dispersion feature 69 may have other forms, including other shapes of cuts and/or perforations through the package material, that extend transversely to the direction of the path 60, added reinforcing strips, tapes, and the like.

FIG. 12A is a perspective view of a package of the present disclosure in a closed configuration, and FIG. 12B shows the package of FIG. 12A in a partially open configuration. Referring to FIGS. 12A and 12B, a package 1 of the present disclosure may comprise a top panel 11 comprising closing gussets 11b, a closing seam 11a, and a closing seam fin 11c. A weakened region 700 may be disposed on at least a portion of the closing seam fin 11c between the closing seam 11a and an interior compartment 702 comprising one or more absorbent articles. The weakened region 700 may traverse at least a portion of the closing gussets 11b. The weakened region 700 may comprise a series of perforations and/or scoring 704. The series of perforations and/or scoring 704 may form a path generally parallel to the closing seam 11a. The path of perforations and/or scoring may have a relatively high cut-to-land ratio. A relatively high cut-to-land ratio may be preferable where the path of perforations and/or scoring traverses at least a portion of the closing gussets because the closing gusset portion comprises four layers of package material, and a higher cut-to-land ratio may reduce the amount of force required to form an opening in the package. For example, the cut-to-land ratio may be between about 0.7:1 and about 6:1, or between about 1:1 and about 6:1, or between about 2:1 and about 6:1, specifically reciting all values within these ranges and any ranges formed therein or thereby.

The weakened region may be configured to form an opening along the path of perforations and/or scoring. The weakened region 700 comprising the series of perforations and/or scoring 704 may be configured such that the closing seam fin 11c is completely removable from the rest of the package 1. In such a configuration, removal of the closing seam fin 11c may result in a large opening—defined by the front 14, back 15, first, and second side panels 12, 13—to allow for easy access to the absorbent article(s) disposed in the interior compartment 702. A further benefit of a large opening created by complete removal of the closing seam fin is that absorbent articles may be configured in any manner within the interior compartment, and still be easily removable.

Figures 13A, 13B:
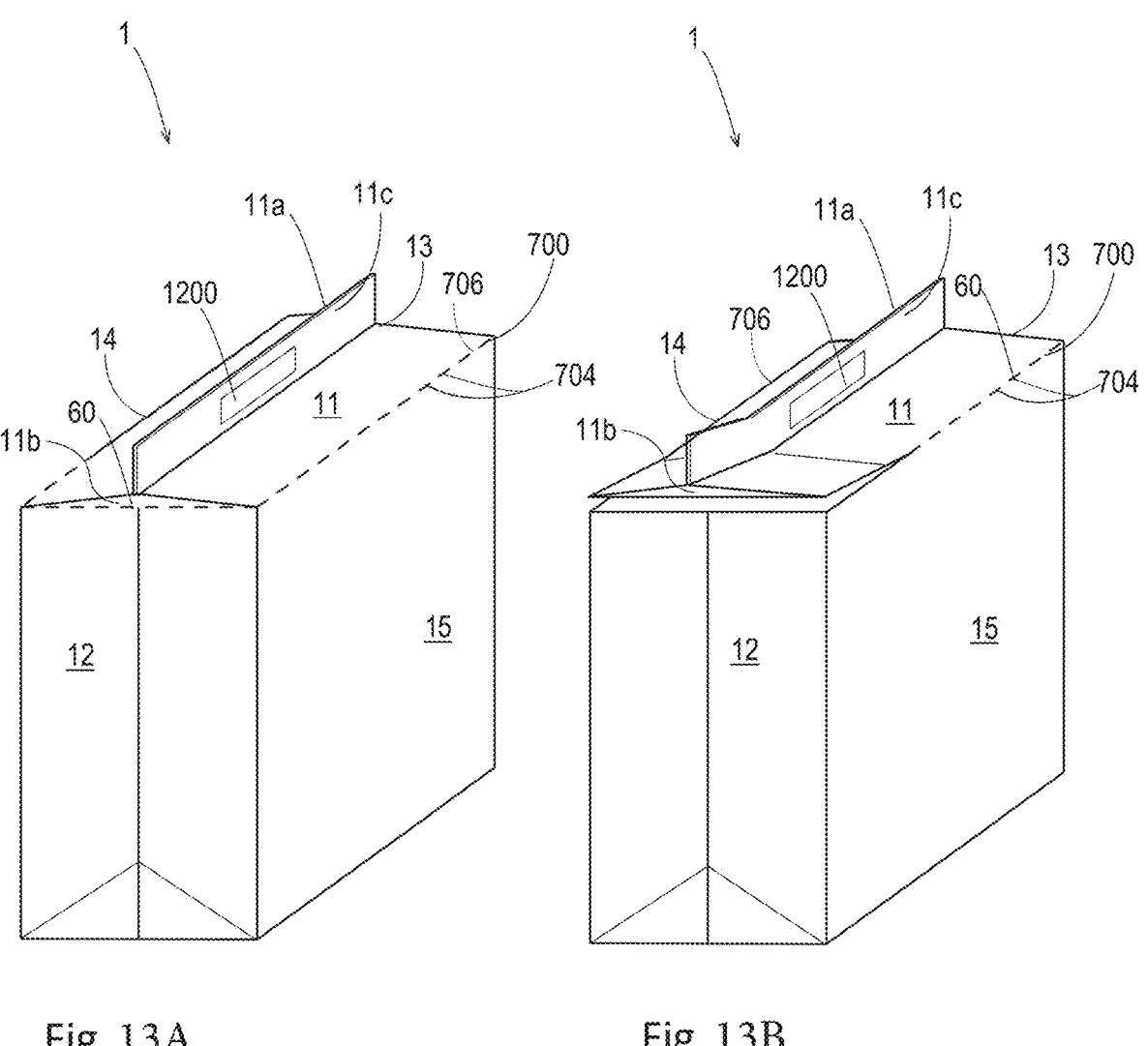
FIG. 13A is a perspective view of a package of the present disclosure, depicting a weakened region disposed on a portion of a top edge of the package.
FIG. 13B depicts the package of FIG. 13A in a partially open configuration.

FIG. 13A is a perspective view of a package of the present disclosure in a closed configuration, and FIG. 13B shows the package of FIG. 13A in a partially open configuration. Referring to FIGS. 13A and 13B, a package 1 of the present disclosure may comprise a weakened region 700 disposed on at least a portion of a top edge region 706 of the package 1 between at least one of: the top panel 11 and the front panel 14, the top panel 11 and the back panel 15, the top panel 11 and the first side panel 12, and the top panel 11 and the second side panel 13. Where the top panel 11 comprises closing gussets 11b, the weakened region 700 may be disposed below the closing gussets 11b. A relatively low cut-to-land ratio may be preferable where the path of perforations and/or scoring does not traverse a portion of the closing gussets, because region of the package outside of the closing gussets only comprises a single layer of package material. For example, the cut-to-land ratio may be between about 0.7:1 and about 6:1, or between about 1:1 and about 5:1, or between about 2:1 and about 4:1, specifically reciting all values within these ranges and any ranges formed therein or thereby.

A package of the present disclosure may comprise a weakened region, wherein the weakened region is disposed on a portion of the top edge region of the package only between the top panel and the front panel or only between the top panel and the back panel. Such a weakened region configuration may be beneficial where articles are disposed within the interior compartment of the package in a tri-fold configuration and arranged such that the fold noses are disposed proximate to the first and second side panels of the package. In such a configuration, the weakened region may form an opening slit about the same size as the article, and may allow only one article at a time to pass through the opening, thus keeping the remaining articles securely and orderly within the package.

A package of the present disclosure may comprise a weakened region that is disposed on a portion of the top edge region of the package only between the top panel and two contiguous panels, such as the front panel and a side panel, or the back panel and a side panel.

A package of the present disclosure may comprise a weakened region that is disposed on a portion of the top edge region of the package only between the top panel and three contiguous panels, such as the front panel and the two side panels, the back panel and the two side panels, or one of the side panels and both the front and back panel. In such a configuration, the weakened region may form an opening that leaves one side of the top panel attached to the remainder of the package, thus forming a hinge. Therefore, the top panel may be removed from above the interior compartment to allow access to all the articles disposed within the package, yet the top panel will remain attached to the package and thus easily available for replacement over the articles.

A package of the present disclosure may comprise a weakened region disposed on a portion of the top edge region of the package between the top panel and the front, back, and both side panels. In such a configuration, the top panel may be completely removable. Such a configuration may create a large opening to allow for easy access to the interior compartment and the articles disposed therein.

Figures 14A, 14B:
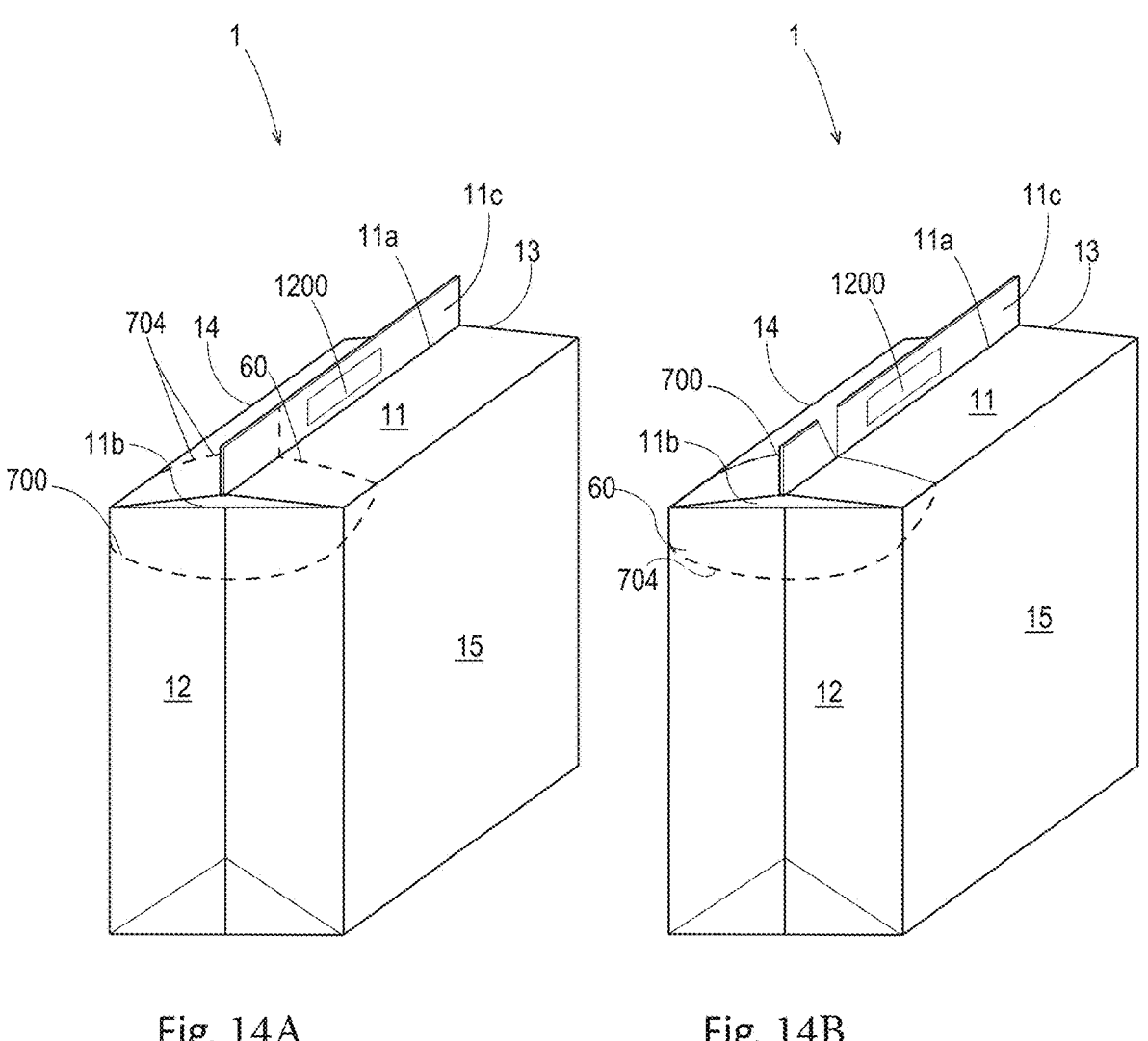
FIG. 14A is a perspective view of a package of the present disclosure, depicting a weakened region surrounding a closing gusset.
FIG. 14B depicts the package of FIG. 14A in a partially open configuration.

Referring to FIGS. 14A and 14B, a package 1 of the present disclosure may comprise a weakened region 700 disposed on at least a portion of the top panel 11, at least a portion of the front panel 14, at least a portion of the back panel 15, and at least a portion of one of the first or second side panels 12, 13. The weakened region may surround a closing gusset 11b. The weakened region may form an opening upon the application of appropriate force from a consumer that may remove the closing gusset 11b. Removal of the closing gusset may form an entry point into the interior compartment of the package approximately the same width as the sides of the package. Such an entry point may be provided for the easy removal of articles that are arranged from side-to-side in the package. The weakened region may comprise a path of perforations and/or scoring with a cut-to-land ratio between about 0.7:1 and about 6:1, or between about 1:1 and about 5:1, or between about 2:1 and about 4:1, specifically reciting all values within these ranges and any ranges formed therein or thereby.

FIG. 15A is a perspective view of a package 1 of the present disclosure comprising a weakened region 700 disposed on at least a portion of at least three of the panels of the package. FIG. 15B shows the package of FIG. 15A in an open configuration. Referring to FIG. 15A, the weakened region may comprise a series of perforations and/or scoring 704 disposed on a portion of each of the at least three panels. The weakened region 700 may comprise a single path of perforations and/or scoring 704 disposed along each of the panels, or as discussed with regard to FIGS. 9A-9E, the weakened region may comprise multiple paths of perforations and/or scoring 704 separated by registered land areas 62. The registered land areas may be disposed at transition areas between panels of the package, such as at the package corners. The weakened region 700 may be disposed on at least three of the front 14, back 15, first side 12, and second side 13 panels, such that the weakened region 700 defines a base 1502 of the package and a hood structure 1504. Referring now to FIG. 15B, it is believed that a hood structure 1504 having three sides, each formed of a portion of one of the front 14, back 15, first side 12, and second side 13 panels, and a top formed of a portion of the top panel 11, may provide an effective, easy to use cover over the supply of unused absorbent articles disposed within the package, and may help guard against entry of airborne contaminants into the package. The hood structure 1504 is formed when the consumer tears the package material along the weakened region 700. Where the weakened region is disposed on only three panels, a portion of the hood structure may be partially removable from the base, since at least one panel may remain intact and attached to the base. After opening, the hood structure 1504 may be reclosed by returning it to a position similar to the one it occupied with respect to the remainder of the package prior to opening.

As shown in FIGS. 15A and 15B, the weakened region 700 may comprise a path or paths of perforations and/or scoring 704 disposed on one of the first or second side panels 12, 13, as well as on portions of both of the front and back panels 14, 15. This configuration (herein designated a "long-short-long" or "LSL" path) forms an opening along an entire short side (either the first or second side) of the package. Such a configuration may be especially useful where the absorbent articles are stacked within the package from side panel to side panel. In such a case, the entire width of the article may be exposed upon opening the package, and the article may be easy to remove. The path(s) of perforations and/or scoring may not traverse the entire width of the front and/or back panels. For example, the path(s) of perforations and/or scoring may traverse about 25 percent, about 33 percent, about 45 percent, about 50 percent, about 60 percent, or about 75 percent of the width of the front and back panels. Referring again to FIGS. 15A and 15B, where the path(s) of perforations and/or scoring 704 do not traverse the entire width of the front and/or back panels, it may be beneficial that a stress dispersion feature 69 be disposed proximate to the endpoint of the path(s) of perforations and/or scoring 704. As discussed, the stress dispersion feature may serve to disperse tearing stresses concentrated at the endpoint, and may help to reduce or prevent the tearing of the package material past the endpoint of the path(s) of perforations and/or scoring. In another example, the path(s) of perforations and/or scoring traverses the entire width of the front and back panels.

Figure 16:
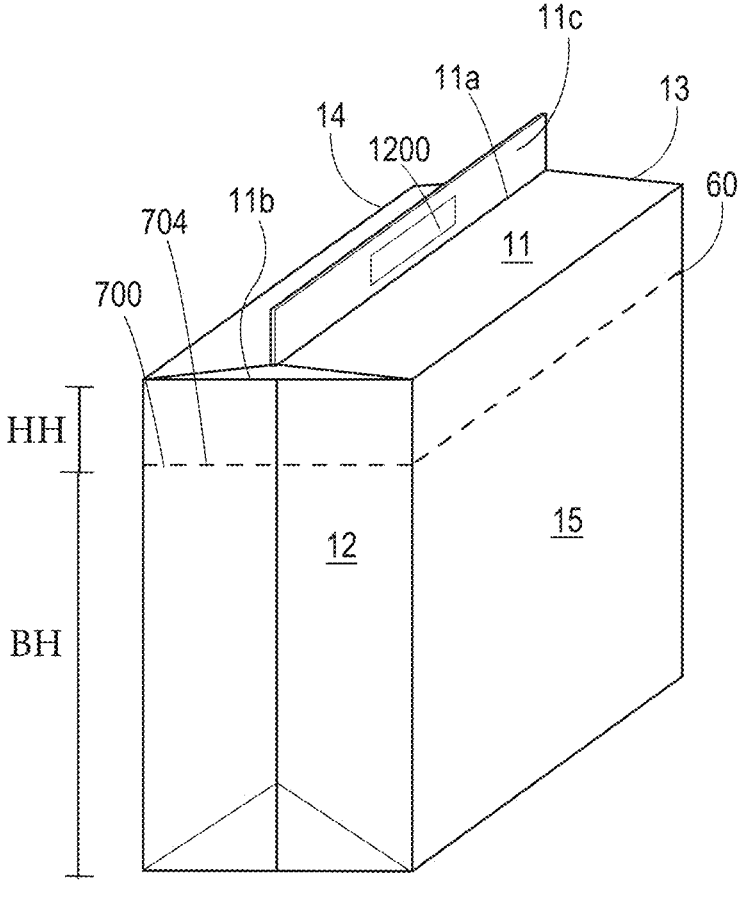
FIG. 16 is a perspective view of a package of the present disclosure, depicting a weakened region disposed on at least a portion of the first side, second side, and one of the front or back panels (short-long-short) and forming a base and a hood.

In another form, shown in FIG. 16, the weakened region 700 may comprise a path or paths of perforations and/or scoring 704 disposed on one of the front or back panels 14, 15, as well as on portions of both of the first and second side panels 12, 13. This configuration (herein designated a "short-long-short" or "SLS" path) is designed to form an opening along an entire long side (either the front or back) of the package. Such a configuration may be especially useful where the articles are stacked within the package from front panel to back panel. In such a case, the entire width of the article may be exposed upon opening the package, and the article may be easy to remove. The path(s)

of perforations and/or scoring traverses the entire width of the side panels. In another form, the path(s) of perforations and/or scoring may not traverse the entire width of the side panels. For example, the path(s) of perforations and/or scoring may traverse about 25 percent, about 33 percent, about 45 percent, about 50 percent, about 60 percent, or about 75 percent of the width of the side panels. The weakened region 700 may comprise a stress dispersion feature disposed proximate to the endpoints of the path(s) of perforations and/or scoring, as discussed relative to FIG. 15.

In a form, the weakened region may be disposed on each of the front, back, first side, and second side panels. The weakened region may comprise a path or paths of perforations and/or scoring that traverse each of the panels. In such a configuration, the hood structure may be completely removable from the base. Such a configuration may be beneficial where the package material has limited flexibility, and is susceptible to tearing.

Referring now to FIGS. 15A, 15B, and 16, the weakened region 700 may be disposed on the at least three panels of the package 1 such that the base 1502 has a base height (BH), and the hood structure 1504 has a hood height (HH). The base height may be from about 60 percent to about 90 percent, from about 65 percent to about 85 percent, or from about 70 percent to about 85 percent of the total height of the package, specifically reciting all values within these ranges and any ranges formed therein or thereby.

It is believed that consumers may prefer the hood structure to have at least a minimum amount of material to grasp and pull back over the unused portion of the absorbent articles in the package. The minimum amount of material may be placed around a portion of the stack of absorbent articles in the package and remain in place until removed again by a user. The packages of the present disclosure may therefore have a hood height (HH) of at least about 15 mm, at least about 20 mm, or at least about 25 mm.

The packages of the present disclosure may be reclosable. The packages may comprise means for reclosing the packages after opening about the weakened region(s). Means for reclosing may be, for example, pressure sensitive adhesive, reclosable zipper, and hook-and-loop fasteners. The means for reclosing the package may be disposed adjacent the weakened region(s).

The packages of the present disclosure may comprise more than one weakened region. Each weakened region may comprise a path or paths of perforations and/or scoring. The multiple paths of perforations and/or scoring may not intersect. The packages of the present disclosure comprise more than one weakened region within the top 50% of the package height.

The packages of the present disclosure may comprise a graphical indicia and/or an identifying colorant to signal to a user the presence of a weakened region. In a form, the weakened region may comprise an identifying colorant. The identifying color may be a color different than a color disposed on a consumer facing panel of the package. The package may also, or instead, comprise a graphical representation, for example a graphic of a pair of scissors, disposed adjacent to the weakened region. The inventors have found that the placement of a graphical indicia and/or an identifying colorant in the weakened region of the packages of the present disclosure may increase the consumer's awareness and delight for the weakened region that is configured to function as an opening feature.

Regardless of the configuration of the weakened region of the packages of the present disclosure, the packages may have a Weakened Region Tensile Strength (WRTS) of at least 1.18 kN/m, or between about 1.18 kN/m and about 8.00 kN/m, between about 1.27 kN/m and about 6.50 kN/m, between about 1.35 kN/m and about 5.00 kN/m, between about 1.49 kN/m and about 4.72 kN/m, between about 1.49 kN/m and about 3.35 kN/m, or between about 1.6 kN/m and about 3.00 kN/m, specifically reciting all values within these ranges and any ranges formed therein or thereby, according to the Strength Tensile Test Method described herein. It is believed that a package comprising a weakened region with a WRTS within the above ranges may be sufficient to withstand unintentional rupturing during package formation, package filling, shipment, and store display.

The inventors have found that packages with a balance between the strength properties of the package material in an unweakened region (Tensile Strength) and the strength properties of the package material in the weakened region (WRTS) may provide a flexible and resilient package that may withstand the rigors of a manufacturing process while also providing for an opening feature that is configured for ease of package opening. This balance may be calculated by taking the ratio of the Weakened Region Tensile Strength (WRTS) of a package versus the Tensile Strength of a portion of the package without a weakened region (according to the Strength Tensile Test Method), herein referred to as the "Weakened Region Performance Factor" (WRP Factor). The packages of the present disclosure may have a WRP Factor of between about 0.14:1 and about 0.98:1, about 0.15:1 and about 0.98:1, about 0.16:1 and about 0.94:1, about 0.18:1 and about 0.94:1, about 0.19:1 and about 0.94:1, about 0.2:1 and about 0.94:1, or about 0.23:1 and about 0.6:1, specifically reciting all values within these ranges and any ranges formed therein or thereby.

Table 2 presents Weakened Region Tensile Strength (WRTS) data from samples various package materials. WRTS and WRP Factor data from weakened region configurations comprising paths of perforations having different cut-to-land ratios and different perforation shapes are presented for each package material. All of the weakened regions of the samples presented in Table 2, with the exception of the "Angled Perf" variable, comprise straight line perforations with a 1 mm land area. The "Angled Perf" variable comprises perforations shaped as shown in FIG. 7E, with an approximate 2.5 mm land area.

Sample 5 is a package material of calendered specialty kraft paper consisting entirely of virgin fibers with a Basis Weight of 70 gsm, available from Mondi™ under the trade name Advantage Smooth White Strong. Various weakened region configurations comprising paths of perforations disposed in the CD of the package material are presented.

Sample 6 is a package material of paper produced from pure, white kraft pulp and consisting entirely of virgin fibers with a Basis Weight of 70 gsm, available from BillerudKorsnäs™. Various weakened region configurations comprising paths of perforations disposed in the CD of the package material are presented.

Sample 7 is a package material of paper produced from pure, white kraft pulp and consisting entirely of virgin fibers with a Basis Weight of 80 gsm, available from BillerudKorsnäs™ under the trade name Axello Tough White. Various weakened region configurations comprising paths of perforations disposed in the CD of the package material are presented.

TABLE 2

| Cut-to-land | Weakened Region Tensile Strength (WRTS) in MD (kN/m) | | | Weakened Region Performance Factor |
| --- | --- | --- | --- | --- |
| Ratio | Maximum | Average | Std. Dev. | (WRP Factor) |
| Sample 5 (70 gsm package material; 8.11 kN/m MD Tensile Strength) | | | | |
| 1:1 | 4.64 | 4.61 | 0.04 | 0.568 |
| 2:1 | 3.01 | 2.66 | 0.41 | 0.328 |
| 3:1 | 2.22 | 2.06 | 0.15 | 0.254 |
| 6:2 | 2.20 | 1.91 | 0.32 | 0.236 |
| 4:1 | 1.97 | 1.70 | 0.37 | 0.210 |
| 6:1 | 1.40 | 1.34 | 0.05 | 0.165 |
| 2.5:1 (Angled Perf.) | 0.63 | 0.59 | 0.04 | 0.073 |
| Sample 6 (70 gsm package material) | | | | |
| 5:1 | 1.62 | 1.27 | 0.03 | NA |
| 6:1 | 0.78 | 0.74 | 0.05 | NA |
| Sample 7 (80 gsm package material; 8.03 kN/m MD Tensile Strength) | | | | |
| 1:1 | 3.98 | 3.44 | 0.46 | 0.428 |
| 2:1 | 2.08 | 1.89 | 0.27 | 0.235 |
| 3:1 | 1.93 | 1.78 | 0.30 | 0.222 |
| 6:2 | 2.07 | 1.76 | 0.28 | 0.219 |
| 4:1 | 1.56 | 1.49 | 0.08 | 0.186 |
| 6:1 | 1.11 | 1.07 | 0.03 | 0.133 |
| 2.5:1 (Angled Perf.) | 0.74 | 0.65 | 0.10 | 0.081 |

As shown in Table 2, the WRTS of the package materials with various weakened region configurations ranges from 0.63 kN/m to 4.64 kN/m. The data suggest a trend whereby the lower cut-to-land ratio configurations exhibit a higher tensile strength as compared to the higher cut-to-land ratio configurations. The weakened regions comprising angled perforations, however, do not follow this trend. The angled perforation-comprising weakened regions exhibit the lowest WRTS. The Weakened Region Performance Factor (WRP Factor) data follow a similar trend as the WRTS data, with the lower cut-to-land ratio configurations exhibiting higher WRP Factor scores.

Table 3 presents tear tensile data from Samples 5 and 7, as described above. The Absolute TearStrength is the force required to tear a single perforation land area within the first 5 perforation land areas of a weakened region, as measured according to the Tear Tensile Test Method described herein. The Relative Tear Strength is the average force required to tear 1 mm of land area over the first 5 perforations land areas of a weakened region, as measured according to the Tear Tensile Test Method described herein. The data may be useful in determining perforation configurations and patterns that may be relatively easy for a consumer to open.

TABLE 3

| Cut-to-Land Ratio | Absolute Tear Strength range (N) | Relative tear Strength: Avg. Force over first 5 land areas (N/mm) | Visual Inspection |
| --- | --- | --- | --- |
| Sample 5 | | | |
| 1:1 | N/A | N/A | Unable to open 5 consecutive lands |
| 2:1 | 0.80-1.56 | 1.03 | All 5 lands opened. |
| 4:1 | 0.81-1.53 | 1.11 | All 5 lands opened. |

TABLE 3-continued

| Cut-to-Land Ratio | Absolute Tear Strength range (N) | Relative tear Strength: Avg. Force over first 5 land areas (N/mm) | Visual Inspection |
| --- | --- | --- | --- |
| 6:1 | 0.86-1.37 | 1.10 | All 5 lands opened. |
| 2.5:1 (Angled Perf.) | 0.84-1.47 | 1.08 | All 5 lands opened. |
| Sample 7 | | | |
| 1:1 | N/A | N/A | Unable to open 5 consecutive lands |
| 2:1 | 0.63-1.36 | 1.02 | All 5 lands opened. |
| 4:1 | 0.634-1.46 | 0.96 | All 5 lands opened. |
| 6:1 | 0.77-1.52 | 1.01 | All 5 lands opened. |
| 2.5:1 (Angled Perf.) | 0.73-1.03 | 0.91 | All 5 lands opened in 1 replicate. Fewer than 5 lands opened in 2 replicates. |

As shown in Table 3, the Absolute Tear Strength range was between 0.63 N and 1.56 N. The Relative Tear Strength was slightly greater for Sample 5 as compared to Sample 7. This is consistent with the WRTS data presented in Table 2, showing the various weakened region configurations disposed in Sample 5 have a slightly greater WRTS than the same configurations disposed in Sample 7. Without wishing to be bound by theory, it is believed that the higher WRTS and Relative Tear Strength of Sample 5, as compared to the same configurations in Sample 7, may be due to the package material of Sample 5 having a slightly higher MD Tensile Strength. The weakened region comprising angled perforations in Sample 7 failed to open 5 consecutive land areas in two replicates. During testing in these two replicates, the tear line diverted from the path of perforations into the unperforated package material.

Regardless of the configuration of the weakened region of the packages of the present disclosure, the weakened region may have an Absolute Tear Strength of between about 0.63 N and about 1.56 N per single perforation land area, between about 0.73 N and about 1.46 per single perforation land area, or between about 0.8 N and about 1.3 N per single perforation land area, according to the Tear Tensile Test Method described herein.

The packages of the present disclosure may comprise a weakened region having a Relative Tear Strength of between about 0.8 N/mm and about 1.3 N/mm, between about 0.9 N/mm and 1.2 N/mm, or between about 0.95 N/mm and about 1.15 N/mm, according to the Tear Tensile Test Method described herein.

The inventors have found, while not wishing to be bound by theory, that process reliability on high speed commercial-scale packaging equipment and acceptable weakened region openability may be simultaneously achieved by appropriately balancing the Weakened Region Tensile Strength (WRTS) and the Tear Strength of the weakened region. Appropriate balancing of these parameters may provide a package that may withstand the rigors of a manufacturing process while also providing for an opening feature that is configured to be opened easily by a consumer with minimal destruction to the unweakened region of the package. This balance may be represented by a Tear Performance (TP) Factor. The TP Factor is defined as the ratio of the package Weakened Region Tensile Strength (WRTS), according to the Strength Tensile Test Method described herein, versus the Absolute Tear Strength of the weakened region of the package, according to the Tear Tensile Test Method described herein. The packages of the present disclosure may have a TP Factor of between about 0.8 and about 5, between about 0.9 and about 4.5, or between about 1 and about 4, specifically reciting all values within these ranges and any ranges formed therein or thereby. It is believed that a package having a TP Factor within the above ranges may exhibit sufficient strength to withstand manufacturing processes while being easily openable about the weakened region with minimal destruction to the unweakened region of the package.

Test Methods

Strength Tensile Test Method

The Strength Tensile Test Method is run according to ASTM D828-16 "Standard Test Method for Tensile Properties of Paper and Paperboard Using Constant-Rate-of-Elongation Apparatus" with the following specifications and/or modifications: Two sets of test specimens are cut from package materials containing a weakened region. The first set of test specimens contain the weakened region, such that the weakened region is disposed the entire way across the width test sample and is centered along and perpendicular to the length of the test specimen. The second set of test specimens are cut from the same package materials and are oriented in the same direction as the first set but do not include a weakened region. The specimen length is about 101.6 mm (4 in.) to allow sufficient specimen for clamping in the instrument grips with a distance between the grips of 50.8 mm (2 in.). The rate of grip separation during the test is 300 mm/min. When placing the test specimens containing the weakened region into the grips for testing, the path of the weakened region is to be centered between the grips and perpendicular to the pull axis of the tensile tester. The average tensile strength of the first specimen set containing the weakened region is reported as the Weakened Region Tensile Strength (WRTS) to the nearest 0.01 kN/m. The average tensile strength of the second specimen set without the weakened region is reported as the Package Tensile Strength (MD or CD) to the nearest 0.01 kN/m.

Weakened Region Performance (WRP) Factor—The Weakened Region Performance Factor is calculated by taking the ratio of the Weakened Region Tensile Strength (WRTS) of a package versus the Tensile Strength of the package measured in the same direction (MD or CD). The factor is calculated according to the following equation and reported to the nearest 0.01 units:

$$WRP \text{ Factor} = \frac{\text{Weakened Region Tensile Strength} \left(\frac{kN}{m}\right)}{\text{Package Tensile Strength} \left(\frac{kN}{m}\right)}$$

Tear Tensile Test Method

The Tear Tensile Test Method is run according to ASTM D2261-13 "Tearing Strength of Fabrics by the Tongue (Single Rip) Procedure (Constant-Rate-of-Extension Tensile Testing Machine), which has been adapted for testing package materials comprising natural materials and a weakened region, with the following specifications and/or modifications: Test specimens are cut from package materials containing a weakened region, such that the path of the weakened region is oriented along the center of the specimen width. The specimen width is 50.4 mm (2 in.), with 25.4 mm (1 in.) on either side of the line of weakened regions. The 75 mm (3 in.) preliminary cut made along the center of the width should not partially cut a land region within the weakened region, such that only whole land regions are torn during the test. A total of five replicate test specimens are prepared. The distance between the clamps is set at 50.4 mm (2 in.) at the start of the test, and a testing speed of 300 mm/min is used. Preconditioning, conditioning, and testing of dry test specimens is performed as specified in ASTM D685-17 "Standard Practice of Conditioning Paper and Paper Products for Testing". Calculation Option 1, Average of Five Highest Peaks, is used to measure the average tear strength (peak force) of each of the first five land areas torn during the test and recorded to the nearest 0.01 N. This procedure is repeated for all five test specimens and the arithmetic mean of the five recorded values is calculated and reported as the Absolute Tear Strength value to the nearest 0.01 N. The Absolute Tear strength value is divided by the average width of all the land areas, which were torn, and peak forces measured during testing, and is reported as the Relative Tear Strength value to the nearest 0.01 N/mm.

Tear Performance Factor (TP Factor)—The Tear Performance Factor is calculated by taking the ratio of the package Weakened Region Tensile Strength (WRTS), according to the Strength Tensile Test Method described herein, versus the Absolute Tear Tensile of the weakened region of the package, according to the Tear Tensile Test Method described herein. The factor is calculated according to the following equation and reported to the nearest 0.01 units:

$$TP \text{ Factor} = \frac{\text{Weakened Region Tensile Strength} \left(\frac{kN}{m}\right)}{\text{Absolute Tear Tensile (N)}}$$

Stretch At Break—Stretch At break is calculated by dividing the Mean Elongation at Break (mm) by the initial test length (test span) of 50.8 mm, and then multiplying by 100. Calculate the stretch at break for the MD replicates and then the CD replicates and report respectively as MD Stretch at Break and CD Stretch at Break to the nearest percent.

Tensile Energy Absorption (TEA)—Tensile Energy Absorption (TEA) is calculated using the following equation:

TEA=(1000*Mean Area Under Curve, mJ)/(width of test sample*initial test length)

where the width of the test sample is 25.4 mm, and the initial test length (test span) is 50.8 mm. Calculate the TEA for the MD replicates and then CD replicates and report respectively as MD TEA and CD TEA to the nearest J/m².

Tensile Energy Absorption (TEA) Index—Tensile Energy Absorption (TEA) Index is calculated using the following equation:

$$TEA \text{ Index} = (TEA)/\text{Basis Weight}$$

where TEA is in units of J/m², and Basis Weight is in units of g/m². Calculate the TEA Index for the MD replicates and then the CD replicates and report respectively as MD TEA Index and CD TEA Index to the nearest J/g.

Burst Strength Test Method

Burst strength is the maximum uniformly distributed pressure that a test sample can withstand. Burst strength is measured in accordance with compendial method ISO 2758 using a test apparatus as described within the method. A suitable instrument is the 13-60 Burst Tester for Paper and Foils available from Testing Machines, Inc (New Castle, DE), or equivalent. The instrument is calibrated and operated as per the manufacturer's instructions. All measurements are performed in a laboratory maintained at 23° C.+/−2° C. and 50%+/−2% relative humidity, and test samples are conditioned in this environment for at least 2 hours prior to testing.

Measurements are made on test samples taken from rolls or sheets of the raw material, or test specimens obtained from a finished package. When excising a test sample from a finished package, use care to not impart any contamination or distortion to the test sample during the process. The test sample must be larger than the clamps used to hold the test sample in the instrument. The test sample should be taken from an area free of folds, wrinkles, or seams.

Measure the burst strength (using a clamping pressure sufficient to prevent slippage during the test, and a pumping rate of 95±15 mL/min) for a total of 10 replicate test samples. For samples that are sided, the side of the test sample that is meant to face the inside of the package faces the pressure when placed into the clamps, and 10 replicates are tested in this orientation. For samples that are balanced (not sided), 5 replicates are tested with the inside of the package facing the pressure and 5 replicates are tested with the outside of the package facing the pressure, and the results are averaged together. Record the pressure at which each test sample bursts to the nearest 0.001 kPa. If the burst pressure is less than 70 kPa, multiple layers of the test material must be used. To obtain the burst strength, divide the burst pressure by the number of layers tested. Calculate the arithmetic mean burst pressure for all replicates and report as Burst Strength to the nearest 0.001 kPa.

Caliper Test Method

The caliper, or thickness, of a single-layer test sample is measured under a static load by a micrometer, in accordance with compendial method ISO 534, with modifications noted herein. All measurements are performed in a laboratory maintained at 23° C.±2° C. and 50%±2% relative humidity and test samples are conditioned in this environment for at least 2 hours prior to testing.

Caliper is measured with a micrometer equipped with a pressure foot capable of exerting a steady pressure of 70 kPa±0.05 kPa onto the test sample. The micrometer is a dead-weight type instrument with readings accurate to 0.1 micron. A suitable instrument is the TMI Digital Micrometer Model 49-56, available from Testing Machines Inc., New Castle, DE, or equivalent. The pressure foot is a flat ground circular movable face with a diameter that is smaller than the test specimen and capable of exerting the required pressure. A suitable pressure foot has a diameter of 16.0 mm. The test sample is supported by a horizontal flat reference platform that is larger than and parallel to the surface of the pressure foot. The system is calibrated and operated per the manufacturer's instructions.

Measurements are made on single-layer test samples taken from rolls or sheets of the raw material, or test samples obtained from a finished package. When excising the test sample from a finished package, use care to not impart any contamination or distortion to the sample during the process. The excised sample should be free from residual adhesive and taken from an area of the package that is free from any seams or folds. The test sample is ideally 200 mm² and must be larger than the pressure foot.

To measure caliper, first zero the micrometer against the horizontal flat reference platform. Place the test sample on the platform with the test location centered below the pressure foot. Gently lower the pressure foot with a descent rate of 3.0 mm per second until the full pressure is exerted onto the test sample. Wait 5 seconds and then record the caliper of the test sample to the nearest 0.1 micron. In like fashion, repeat for a total of ten replicate test samples. Calculate the arithmetic mean for all caliper measurements and report the value as Caliper to the nearest 0.1 micron.

Basis Weight Test Method

The basis weight of a test sample is the mass (in grams) per unit area (in square meters) of a single layer of material and is measured in accordance with compendial method ISO 536. The mass of the test sample is cut to a known area, and the mass of the sample is determined using an analytical balance accurate to 0.0001 grams. All measurements are performed in a laboratory maintained at 23° C.±2° C. and 50%±2% relative humidity and test samples are conditioned in this environment for at least 2 hours prior to testing.

Measurements are made on test samples taken from rolls or sheets of the raw material, or test samples obtained from a finished package. When excising the test sample from a finished package, use care to not impart any contamination or distortion to the sample during the process. The excised sample should be free from residual adhesive and taken from an area of the package that is free from any seams or folds. The test sample must be as large as possible so that any inherent material variability is accounted for.

Measure the dimensions of the single layer test sample using a calibrated steel metal ruler traceable to NIST, or equivalent. Calculate the Area of the test sample and record to the nearest 0.0001 square meter. Use an analytical balance to obtain the Mass of the test sample and record to the nearest 0.0001 gram. Calculate Basis Weight by dividing Mass (in grams) by Area (in square meters) and record to the nearest 0.01 grams per square meter (gsm). In like fashion, repeat for a total of ten replicate test samples. Calculate the arithmetic mean for Basis Weight and report to the nearest 0.01 grams/square meter.

In-Bag Stack Height Test Method

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e., each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 230±2° C. and 50±5% relative humidity prior to measurement.

The horizontal sliding plate is raised, and an absorbent article package is placed centrally under the horizontal sliding plate in such a way that the absorbent articles within the package are in a horizontal orientation (see FIG. 6). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured, and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Combinations:

1. A package of one or more absorbent articles comprising:

a package material comprising natural fibers;

wherein the package material forms a front panel, a back panel opposite the front panel, a first side panel, a second side panel opposite the first side panel, a top panel, and a bottom panel opposite the top panel, wherein the panels define an interior compartment of the package, and wherein the one or more absorbent articles are disposed in the interior compartment;

wherein the package material has a Basis Weight between about 50 gsm and about 120 gsm, preferably between about 55 gsm and about 115 gsm, more preferably between about 60 gsm and about 110 gsm, according to the Basis Weight Test Method;

wherein the package comprises a weakened region in the package material configured to form an opening; and wherein the package is sealed such that the one or more absorbent articles are enclosed within the interior compartment.

2. A package of one or more absorbent articles comprising:

a package material comprising natural fibers;

wherein the package material forms a front panel, a back panel opposite the front panel, a first side panel, a second side panel opposite the first side panel, a top panel, and a bottom panel opposite the top panel, and wherein the panels define an interior compartment;

wherein the package is sealed such that the one or more absorbent articles are enclosed within the interior compartment;

wherein the package material has a Basis Weight between about 50 gsm and about 120 gsm, preferably between about 55 gsm and about 115 gsm, more preferably between about 60 gsm and about 110 gsm, according to the Basis Weight Test Method;

wherein the package comprises a weakened region, wherein the weakened region forms at least a portion of an opening feature; and wherein the package has a Weakened Region Performance Factor of between about 0.14:1 and about 0.98:1, according to the Strength Tensile Test Method.

3. The package of Paragraphs 1 or 2, wherein the package material has a MD Tensile Strength of at least 5.0 kN/m, preferably at least 7.0 kN/m, more preferably at least 8.0 kN/m, according to the Strength Tensile Test Method.

4. The package of any of the preceding Paragraphs, wherein the package material has a CD Tensile Strength of at least 3 kN/m, preferably at least 4 kN/m, or more preferably at least 5.5 kN/m, according to the Strength Tensile Test Method.

5. The package of any of the preceding Paragraphs, wherein the package material has an MD Stretch At Break of between about 3 percent and about 6.5 percent, preferably between about 3.2 percent and about 6.2 percent, more preferably between about 3.5 and about 6 percent, according to the Strength Tensile Test Method.

6. The package of any of the preceding Paragraphs, wherein the package material has a CD Stretch At Break of between about 4 percent and about 10 percent, preferably between about 4.5 percent and about 9.5 percent, more preferably between about 5 percent and about 9 percent, according to the Strength Tensile Test Method.

7. The package of any of the preceding Paragraphs, wherein the package material has a Caliper of between about 50 μm and about 110 μm, preferably between about 55 μm and about 105 μm, more preferably between about 60 μm and about 100 μm, according to the Caliper Test Method.

8. The package of any of the preceding Paragraphs, wherein the package material comprises at least 50 percent by weight natural fibers, preferably at least 70 percent by weight natural fibers, more preferably at least 90 percent by weight natural fibers.

9. The package of any of the preceding Paragraphs, wherein the natural fibers of the package material comprise: cellulose-based fibers, bamboo fibers, cotton, abaca, kenaf, sabai grass, flax, esparto grass, straw, jute, hemp, bagasse, milkweed floss fibers, pineapple leaf fibers, wood fibers, pulp fibers, or combinations thereof.

10. The package of any of the preceding Paragraphs, wherein the package material is paper.

11. The package of any of the preceding Paragraphs, wherein the package is free of a barrier layer.

12. The package of any of the preceding Paragraphs, wherein all of the panels of the package comprise a unitary piece of package material.

13. The package of any of the preceding Paragraphs, wherein the top panel comprises closing gussets, a closing seam, and a closing seam fin extending from the closing seam.

14. The package of Paragraph 13, wherein at least a portion of the closing seam fin is releasably attached to a portion of the top panel.

15. The package of any of Paragraphs 13 or 14, wherein the weakened region is disposed between the closing seam and the interior compartment, and wherein the weakened region traverses at least a portion of one of the closing gussets.

16. The package of any of Paragraphs 13-15, wherein the weakened region comprises a series of perforations and/or scoring.

17. The package of Paragraph 16, wherein the series of perforations and/or scoring forms a path generally parallel to the closing seam, and wherein a path formed by the series of perforations and/or scoring has a cut-to-land ratio of between about 0.7:1 and about 6:1, preferably between about 0.85:1 and about 6:1, more preferably between about 1:1 and about 6:1, even more preferably between about 2:1 and about 4:1.

18. The package of any of Paragraphs 1-14, wherein the weakened region is disposed on at least a portion of a top edge region of the package between at least one of: the top panel and the front panel, and the top panel and the back panel.

19. The package of Paragraph 18, wherein the weakened region is further disposed on at least a portion of the top edge region of the package between at least one of: the top panel and the first side panel, and the top panel and the second side panel.

20. The package of any of Paragraphs 18 or 19, wherein the top panel comprises closing gussets and a closing seam, and wherein the weakened region does not traverse the closing gussets.

21. The package of any of Paragraphs 18-20, wherein the weakened region comprises a series of perforations and/or scoring.

22. The package of Paragraph 21, wherein a path formed by the series of perforations and/or scoring has a cut-to-land ratio of between about 0.7:1 and about 6:1, preferably between about 0.85:1 and about 6:1, more preferably between about 1:1 and about 6:1, even more preferably between about 2:1 and about 4:1.

23. The package of any of Paragraphs 1-14, wherein the weakened region is disposed on at least a portion of three of the panels of the package.

24. The package of Paragraph 23, wherein the weakened region is disposed on the front, first side, and second side panels.

25. The package of Paragraph 23, wherein the weakened region is disposed on the front, back, and first side panels.

26. The package of Paragraph 23, wherein the weakened region is disposed on the front, back, and second side panels.

27. The package of Paragraph 23, wherein the weakened region is disposed on the back, first side, and second side panels.

28. The package of any of Paragraphs 23-27, wherein the weakened region comprises a series of perforations and/or scoring.

29. The package of Paragraph 28, wherein the package material comprises a machine direction (MD) and a cross-machine direction (CD), wherein the series of perforations and/or scoring comprises a plurality of cut lines, wherein each cut line comprises at least a portion of the cut line disposed at an angle to the machine direction (MD) or the cross-machine direction (CD), and wherein the angle is between about 200 and about 90°.

30. The package of any of Paragraphs 28-29, wherein a path formed by the series of perforations and/or scoring has a cut-to-land ratio of between about 0.7:1 and about 6:1, preferably between about 0.85:1 and about 6:1, more preferably between about 1:1 and about 6:1, even more preferably between about 2:1 and about 4:1.

31. The package of any of Paragraphs 23-30, wherein the top panel comprises closing gussets and a closing seam, and wherein the weakened region does not traverse the closing gussets.

32. The package of any of the preceding Paragraphs, wherein the package material is recyclable, and wherein the package material exhibits a recyclable percentage of at least 70 percent, more preferably at least 80 percent, or most preferably at least 90 percent, as determined by PTS-RH:021/97 (Draft October 2019) method.

33. The package of any of the preceding Paragraphs, wherein the bottom panel comprises a pinch bottom configuration.

34. The package of any of Paragraphs 1-32, wherein the bottom panel comprises a block bottom configuration.

35. The package of any of Paragraphs 1-32, wherein the bottom panel comprises a cross bottom configuration.

36. The package of any of the preceding Paragraphs, wherein the weakened region comprises a graphical indicia.

37. The package of any of Paragraphs 1-35 further comprising a background color, wherein the weakened region comprises an identifying color, and wherein the identifying color is different than the background color.

38. The package of any of the preceding Paragraphs, wherein the package has a Weakened Region Tensile Strength of between about 1.18 kN/m and about 8.00 kN/m, preferably between about 1.27 kN/m and about 6.50 kN/m, more preferably between about 1.6 kN/m and about 3.00 kN/m, according to the Strength Tensile Test Method.

39. The package of any of the preceding Paragraphs, wherein the package has a Relative Tear Strength of between about 0.8 N/mm and about 1.3 N/mm, preferably between about 0.9 N/mm and 1.2 N/mm, more preferably between about 0.95 N/mm and about 1.15 N/mm, according to the Tear Tensile Test Method.

40. The package of any of the preceding Paragraphs, wherein the package has a Tear Performance Factor of between about 0.865 and about 5.16, preferably between about 0.95 and about 4.55, more preferably between about 1.04 and about 4.06, according to the Tear Tensile Test Method.

41. The package of any of the preceding Paragraphs, wherein the package is formed from a single ply of the package material.

42. A package of one or more absorbent articles comprising:
   a package material comprising natural fibers;
   wherein the package material has a Basis Weight between about 50 gsm and about 120 gsm, preferably between about 55 gsm and about 115 gsm, more preferably between about 60 gsm and about 110 gsm, according to the Basis Weight Test Method;

wherein the package material forms a consumer-facing panel, an opposing back panel, a pair of end seals, and a hoop seam extending between and joining the end seals, and wherein the panels define an interior compartment of the package;

wherein the package comprises a weakened region in the package material configured to form an opening; and wherein the package is sealed such that the one or more absorbent articles are enclosed within the interior compartment.

43. The package of Paragraph 42, wherein the back panel further comprises a closing seam fin extending from the hoop seam, and wherein at least a portion of the closing seam fin is releasably joined to a portion of the back panel.

What is claimed is:

1. A package of one or more absorbent articles comprising:

a package material comprising natural fibers;

wherein the package material forms a front panel, a back panel opposite the front panel, a first side panel, a second side panel opposite the first side panel, a top panel, and a bottom panel opposite the top panel, wherein the panels define an interior compartment of the package, and wherein the one or more absorbent articles are disposed in the interior compartment;

wherein the package material has a Basis Weight between 50 gsm and 120 gsm, wherein the Basis Weight is defined as mass per unit area;

wherein the package comprises a weakened region comprising perforations disposed in the package material configured to form an opening;

wherein the weakened region is disposed on at least a portion of the top panel or a top edge region of the top panel;

wherein the package is sealed such that the one or more absorbent articles are enclosed within the interior compartment;

wherein the package has a Weakened Region Performance Factor of between 0.14:1 and 0.98:1, according to the Strength Tensile Test Method.

2. The package of claim 1, wherein the package material comprises at least 50 percent by weight natural fibers.

3. The package of claim 1, wherein all of the panels of the package are formed from a unitary piece of package material.

4. The package of claim 1, wherein the top panel comprises closing gussets, a closing seam, and a closing seam fin extending from the closing seam.

5. The package of claim 4, wherein the weakened region is disposed between the closing seam and the interior compartment.

6. The package of claim 1, wherein the weakened region is disposed on at least the portion of the top edge region of the package between at least one of: the top panel and the front panel, and the top panel and the back panel.

7. The package of claim 1, wherein the weakened region is disposed on at least a portion of three of the panels of the package.

8. The package of claim 7, wherein the weakened region is disposed on the front, back, and first side panels.

9. The package of claim 1, wherein the package has a Weakened Region Tensile Strength of between 1.18 kN/m and 8.00 kN/m, according to the Strength Tensile Test Method.

10. The package of claim 1, wherein the package has a Relative Tear Strength of between 0.8 N/mm and 1.3 N/mm, according to the Tear Tensile Test Method.

11. The package of claim 1, wherein the package exhibits a recyclable percentage of between about 70 percent to about 99.9 percent as determined by the PTS-RH:021/97 (Draft October 2019), under category II, test method.

12. The package of claim 1, wherein the package material is recyclable, and wherein the package material exhibits a recyclable percentage of at least 70 percent, as determined by PTS-RH:021/97 (Draft October 2019) method.

13. The package of claim 1, wherein the package is formed from a single ply of the package material.

14. The package of claim 1, wherein the package material is free of a barrier layer.

15. The package of claim 1, wherein the package material comprises a barrier layer.

16. The package of claim 15, wherein the barrier layer forms less than 30 percent by weight of the package material.

17. A package of one or more absorbent articles comprising:

a package material comprising natural fibers;

wherein the package material forms a front panel, a back panel opposite the front panel, a first side panel, a second side panel opposite the first side panel, a top panel, and a bottom panel opposite the top panel, wherein the panels define an interior compartment of the package, and wherein the one or more absorbent articles are disposed in the interior compartment;

wherein the package material has a Basis Weight between 50 gsm and 120 gsm, wherein the Basis Weight is defined as mass per unit area;

wherein the package comprises a weakened region comprising perforations disposed in the package material configured to form an opening;

wherein the weakened region is disposed on at least a portion of the top panel or a top edge region of the top panel;

wherein the package is sealed such that the one or more absorbent articles are enclosed within the interior compartment;

wherein the package has a Weakened Region Performance Factor of between 0.14:1 and 0.98:1, according to the Strength Tensile Test Method, and a Tear Performance Factor of between 0.865 and 5.16, according to the Tear Tensile Test Method.

18. The package of claim 17, wherein the package exhibits a recyclable percentage of between about 70 percent to about 99.9 percent as determined by the PTS-RH:021/97 (Draft October 2019), under category II, test method.

19. The package of claim 17, wherein the package material comprises at least 50 percent by weight natural fibers.

20. The package of claim 17, wherein the top panel comprises closing gussets, a closing seam, and a closing seam fin extending from the closing seam, wherein the weakened region is disposed between the closing seam and the interior compartment.

* * * * *